US008029505B2

United States Patent
Hearn et al.

(10) Patent No.: US 8,029,505 B2
(45) Date of Patent: Oct. 4, 2011

(54) EXTERNAL FIXATION SYSTEM AND METHOD OF USE

(75) Inventors: Jim Hearn, Coatsville, PA (US); Thomas J. Maughan, Downingtown, PA (US); Timothy J. Horan, Royersford, PA (US); Michael J. Wahl, Wilmington, DE (US)

(73) Assignee: Synthes USA, LLC, West Chester, PA (US)

( * ) Notice: Subject to any disclaimer, the term of this patent is extended or adjusted under 35 U.S.C. 154(b) by 759 days.

(21) Appl. No.: 11/213,030

(22) Filed: Aug. 25, 2005

(65) Prior Publication Data

US 2007/0049930 A1    Mar. 1, 2007

(51) Int. Cl.
*A61B 17/00* (2006.01)

(52) U.S. Cl. .............................. 606/56; 606/277; 606/59

(58) Field of Classification Search .................... 606/54, 606/55, 56, 57, 58, 59, 250, 251, 252, 253, 606/254, 255, 256, 257, 258, 259, 260, 261, 606/262, 263, 264, 265, 266, 267, 268, 270, 606/271, 272, 273, 274, 275, 276, 277, 278, 606/324; 403/373, 374.3, 398, 400; 411/544; 24/486, 569, 135 R, 135 N See application file for complete search history.

(56) References Cited

U.S. PATENT DOCUMENTS

| | | | | |
|---|---|---|---|---|
| 4,483,334 A | * | 11/1984 | Murray | 606/59 |
| 5,062,844 A | * | 11/1991 | Jamison et al. | 606/54 |
| 5,087,258 A | * | 2/1992 | Schewior | 606/56 |
| 5,540,686 A | * | 7/1996 | Zippel et al. | 606/56 |
| 5,624,440 A | * | 4/1997 | Huebner | 606/59 |
| 5,681,309 A | * | 10/1997 | Ross et al. | 606/56 |
| 5,752,954 A | * | 5/1998 | Mata et al. | 606/59 |
| 5,810,814 A | * | 9/1998 | Newson | 606/59 |
| 5,928,230 A | * | 7/1999 | Tosic | 606/57 |
| 6,022,348 A | | 2/2000 | Spitzer | |

(Continued)

FOREIGN PATENT DOCUMENTS

EP    0 194 187    9/1986

*Primary Examiner* — Eduardo C Robert
*Assistant Examiner* — Jan Christopher Merene
(74) *Attorney, Agent, or Firm* — Fay Kaplun & Marcin, LLP

(57) ABSTRACT

An external fixation system for connecting one or more bone segments together to facilitate healing of bone. The system may include one or more rings and/or ring segments. One or more linear distractors and/or angular distractors may connect the rings to each other so as to allow for distraction and/or reduction/compression of a bone. Linear distractors may enable an operator to move the rings towards and away from each other, while angular distractors may enable an operator to angle the rings relative to each other. In an embodiment using angular distractors, one or more angular separation assemblies may be positioned between the rings. These separation assemblies may have joints which may two portions which may be angled relative to each other and connected directly or indirectly to the rings. Various fasteners (e.g., nuts) and/or tightening members may configured for quick movement along and selective tightening to various components. Moreover, clamps may be attached to the rings and may engage pins, wire, rods, which may be inserted into bone to hold bone segments to each other. The components of the external fixation system may be provided in sets or kits so that the a surgeon may select various combinations of components to create an external fixation system which is configured specifically for the particular needs of a patient and the bone fracture/deformity.

18 Claims, 13 Drawing Sheets

U.S. PATENT DOCUMENTS

| | | |
|---|---|---|
| 6,030,386 A * | 2/2000 | Taylor et al. .................... 606/56 |
| 6,113,599 A * | 9/2000 | Landsberger .................... 606/60 |
| 6,277,119 B1 * | 8/2001 | Walulik et al. .................. 606/57 |
| 6,652,523 B1 * | 11/2003 | Evrard et al. .................... 606/54 |
| 6,702,814 B2 * | 3/2004 | Walulik et al. .................. 606/57 |
| 7,241,074 B2 * | 7/2007 | Thomke et al. ............... 403/385 |
| 2002/0042613 A1 | 4/2002 | Mata |
| 2003/0144609 A1 * | 7/2003 | Kennedy ....................... 600/583 |
| 2003/0181911 A1 * | 9/2003 | Venturini ....................... 606/56 |
| 2003/0187432 A1 | 10/2003 | Johnson |
| 2004/0073212 A1 | 4/2004 | Kim |
| 2006/0177263 A1 * | 8/2006 | Thomke et al. ............ 403/322.4 |
| 2007/0038217 A1 * | 2/2007 | Brown et al. ................... 606/57 |
| 2009/0036891 A1 * | 2/2009 | Brown et al. ................... 606/57 |
| 2010/0298827 A1 * | 11/2010 | Cremer et al. .................. 606/54 |
| 2011/0087226 A1 * | 4/2011 | Murner et al. .................. 606/54 |

* cited by examiner

EXTERNAL FIXATION SYSTEM AND METHOD OF USE

FIELD OF THE INVENTION

The present invention relates to bone fixation system and devices and, in particular, an external fixation device for stabilizing bone segments and promoting repair of bones and its method of use.

BACKGROUND OF THE INVENTION

External fixation devices are used to stabilize bone segments and to facilitate the healing of bones at a bone repair site. As used herein "bone repair site" refers to any bone region which is bounded on at least one side by a relatively healthy bone region to which orthopedic devices can be secured, such as an osteotomy defect or a fracture. Distraction and reduction/compression devices may be incorporated into an external fixation device and may be used to gradually adjust the relative orientation and spacing of the bone parts on opposing sides of a bone repair site.

External fixation devices traditionally include a bar(s), rod(s) and/or arcuate ring(s) as well as transcutaneous pins, screws and/or wires, which are inserted into bone on either side of the bone repair site. Clamps are used to attach the pins, screws and/or wires to the bar(s), rod(s) and/or arcuate ring(s). These clamps may be used to adjust the relative positions of the pins, screws or wires relative to each other as well as the bar(s), rod(s) and/or arcuate ring(s) so that bone segments may be aligned at the bone repair site. When the desired alignment is achieved, the clamps are locked in place to maintain the alignment of bone segments.

Distraction and reduction/compression devices may allow for adjustment of the distance between components attached on opposing sides of a bone repair site. A typical distraction procedure involves at most an osteotomy completely separating the bone into two segments, or at least an incision of the cortical portion of the bone. A distraction device moves components of the fixation device in order to gradually separate the bone segments on either side of the osteotomy (or the medullary or cancellous portion of the bone on either side of the incision). This gradual separation allows new bone to form in the osteotomy void. In other cases, reduction or compression across a bone repair site to hold bone portions together is desired to facilitate healing. Such adjustments, whether distraction or reduction/compression, typically follow a prescribed protocol. After each adjustment, the distraction/reduction/compression device is held fixed and the new bone growth gains strength. After the bone repair site has healed, the external fixation device is removed from the patient.

Existing distraction/reduction/compression devices employ adjustment mechanisms which may be awkward, slow and difficult to adjust in an incremental and reliable fashion. For example, hex nuts or similar conventional fasteners engaged with a threaded bolt or rod are often used to secure components of an external fixation device. These fasteners are assembled and adjusted using a wrench or other tool. Patients and their non-physician caregivers are often tasked with adjusting an external fixation device according to a specific treatment protocol. However, the complexity of existing systems can often lead to improper adjustments, non-compliance or deviation from the prescribed protocol, and/or undue discomfort for the patient.

Accordingly, it is desirable to provide external fixation devices, methods and kits having improved distraction and connection assemblies for stabilizing bone segments and for providing simple and reliable incremental adjustments.

SUMMARY OF THE INVENTION

An external fixation system may include ring assemblies and/or ring segments which may be attached, for example, by one or more linear distractors, angular distractors and/or elongated members. The linear distractors may allow for incremental changes in distance between the ring assemblies and/or ring segments and, thus, may enable distraction/reduction/compression of bone or bone segments.

Each linear distractor may have a body portion, an adjustment knob and an elongated member (e.g., a threaded rod). The body portion may be attached to one ring assembly/segment, the elongated member may be attached to another ring assembly/segment. An end of the elongated member may be moveable positioned within the body portion. The knob may be connected to the body portion so that the knob may rotate relative to the body portion but may be fixed axially. Rotation of the knob may cause the elongated member to move relative to the knob and within the body portion. The body portion may have a window for viewing the position of an end of the elongated member within the body portion. The body portion may also have a gauge which may comprise a scale so as to provide the operator with a visual indication of the movement of the elongated member. Moreover, the knob may have a detent mechanism which may engage one or more indentations positioned around the body portion. Such a construction may provide tactile and/or audible indications to an operator of incremental movements of the distractor and, consequently, of the ring assemblies/segments relative to each other.

Selectively engageable fasteners may also be provided as part of an external fixation system and may allow for rapid assembly and adjustment of the external fixation system. In one embodiment, the selectively engageable fastener may be a nut which may have an axis, a first end, a second end and a bore extending from the first end to the second end. The bore may have an axis which may be oblique to the axis of the nut. The nut may have a first internal threaded portion proximate the first end, a second internal threaded portion proximate the second end and an unthreaded portion between the first and second ends. The nut may be configured such that alignment of the axis of the bore with the axis of a threaded rod may enable an operator to quickly move the nut along the axis of the rod without the need to rotate the nut. In such an orientation, the threaded portions of the nut may not engage the threads of the rod. Alignment of the axis of the nut with the axis of the rod may result in the internal threaded portions of the nut engaging the external threads of the rod so that the nut may be rotated on the rod and tightened against a component of the external fixation system such as a ring assembly/segment. In an alternative embodiment, the threaded portions may be configured in such a way that alignment of axis of the nut with the axis of the rod may allow for quick axial movement of the nut whereas alignment of the axis of the bore with the axis of the rod may engage the threaded portions of the nut with the threads of the rod.

In another embodiment, the selectively engageable fastener may have a body portion with an opening therethrough and a passageway which may have a wall which may be oriented substantially perpendicular to the opening for receiving a threaded member. The selectively engageable fastener may also have an inner member which may be positioned within the body portion. The inner member may have a bore therethrough, which may include a threaded portion and an unthreaded portion. The bore may be sized and configured to receive the threaded member. The inner member may be moveable between a first position and a second position. In the first position, the threaded portion of the inner member may engage the threaded member. Moreover, the threaded member may be held between the threaded portion of the inner member and the wall of the passageway. In the second position, the threaded portion of the inner member may be disengaged from the threaded member so that the tightening member may be freely moveable along an axis of the threaded member.

In order to angle one component of the external fixation system with respect to another component (e.g., angling a threaded rod relative to a ring assembly), a washer assembly may be provided. The washer assembly may have a male washer having a bore therethrough and a convex surface and a female washer having a bore therethrough and a concave surface. The convex surface of the male washer may move within the concave surface of the female washer. The female washer may have a flat surface for positioning against a component, for example, a ring assembly/segment. The male washer may also have a flat surface for engagement with a nut which may be used to tighten the washer assembly against a surface of a component of the system.

An angular distractor may be another component which may enable an operator to angle one component of an external fixation system relative to another component. For example, an angular distractor may be used to angle a threaded rod relative to a ring assembly/segment. In one embodiment, the angular distractor may comprise a first connector and a second connector, the first and second connector may be sized and configured to engage a first ring member and a second ring member, respectively. The angular distractor may also have a rod with a proximal end and a distal end. The second connector may rotatably connect the rod to a second ring member. The knob may have a bore therethrough and may be operably connected to the first connector and the distal end of the rod such that rotation of the knob may cause the rod to move axially through the bore of the knob. The first connector may rotatably connect the knob to the first ring member and the knob may rotate with respect to the first connector.

In an embodiment using an angular distractor, the external fixation system may have one or more angular separation assemblies being sized and configured to be operably connected to a ring assembly/segment. An angular separation assembly may have a first body portion and a second body portion, wherein the first and second body portions may be operably connected to each other such that the body portions may rotate relative to each other. The body portions may be connected directly to a ring assembly/segment. Alternatively, a first rod may be operably connected to one or both of the first and second body portions and may connect the body portions to a ring assembly/segment. In one embodiment, one of the first and second body portions may have a ball portion and the other of the first and second body portions may have a socket for receiving the ball such that the first and second body portions may be polyaxially moveable relative to each other.

An external fixation system may also incorporate one or more clamps to engage bone connection elements (e.g., pins, wires and screws) which may be inserted into bone. The clamp may have a base portion, a first vise plate, a second vise plate and a fastener which may connect the first and second vise plates to the base portion. The vise plates may be sized and configured to receive a bone connection element therebetween. In one embodiment, the second vise plate may have an engagement portion (e.g., serrations) for engaging a corresponding engagement portion (e.g., serrations) on the base.

The fastener may be positioned through the first and second vise plates and may engage the base. A first biasing member may be positioned between the fastener and the first vise plate, and a second biasing member may be positioned between the second vise plate and the base for separating the engagement portions of the second vise plate and the base. The second biasing member may be compressible to allow the engagement portions to engage each other upon tightening of the fastener to the base.

Any, all or selected devices describe herein such as, for example, the ring assemblies, ring segments, linear distractors, nuts, tightening members, rods, washers, angular distractors, angular separation assemblies, clamps, bone connection elements (e.g., pins, wires and/or screws), fasteners (e.g., nuts, bolts, rivets, etc) and/or components of any of the devices may be provided in sets or kits so that the a surgeon may select various combinations of components to create an external fixation system which is configured specifically for the particular needs of a patient and the bone fracture/deformity. It should be noted that one or more of each device and/or their components may be provided in a kit or system. In some kits or sets, the same device may be provided in different shapes and/or sizes (e.g., multiple rods of different lengths and/or multiple clamps, distractors, nuts of different sizes).

BRIEF DESCRIPTION OF THE DRAWINGS

The external fixation system, its components and the method of use are explained in even greater detail in the following exemplary drawings. The external fixation system, its components and method of operation and use may be better understood by reference to the following drawings, wherein like references numerals represent like elements. The drawings are merely exemplary to illustrate the structure, operation and method of use of the external fixation device and it components and certain features that may be used singularly or in combination with other features and the invention should not be limited to the embodiments shown.

DETAILED DESCRIPTION

Figure 1:
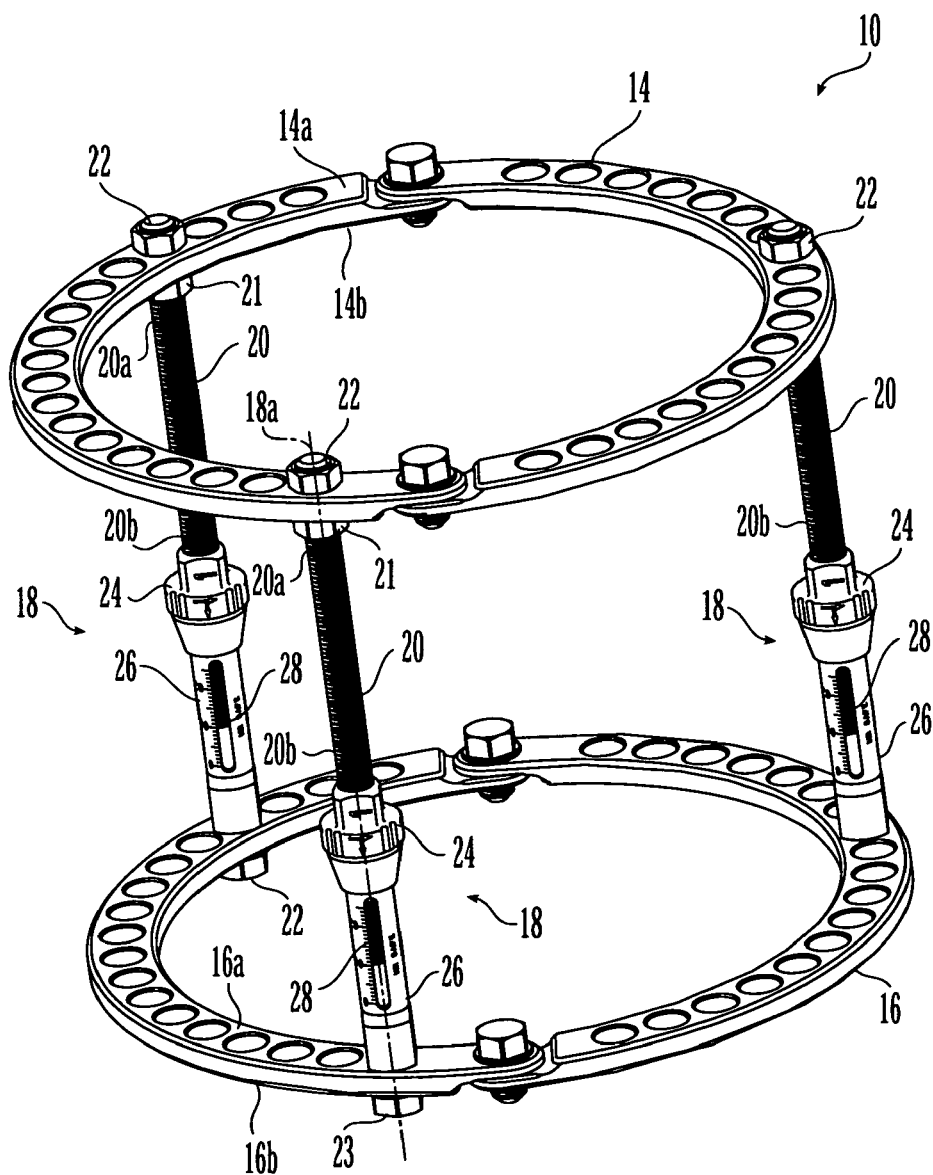
FIG. 1 is a perspective view of an exemplary embodiment of an external fixation system of the present invention.

As shown in FIG. 1, the external fixation system 10 may include a first ring assembly 14 and a second ring assembly 16, which may be operably attached to and separated by one or more linear distractors 18. In some embodiments, the external fixation system 10 may have more than two ring assemblies. Moreover, in one preferred embodiment, three linear distractors 18 may be used to connect two ring assemblies (e.g., ring assemblies 14, 16), although other number of linear distractors may be used and other component in addition to or alternatively may be used to attach and separate ring assemblies, such as ring assembly 14, 16.

Figure 2:
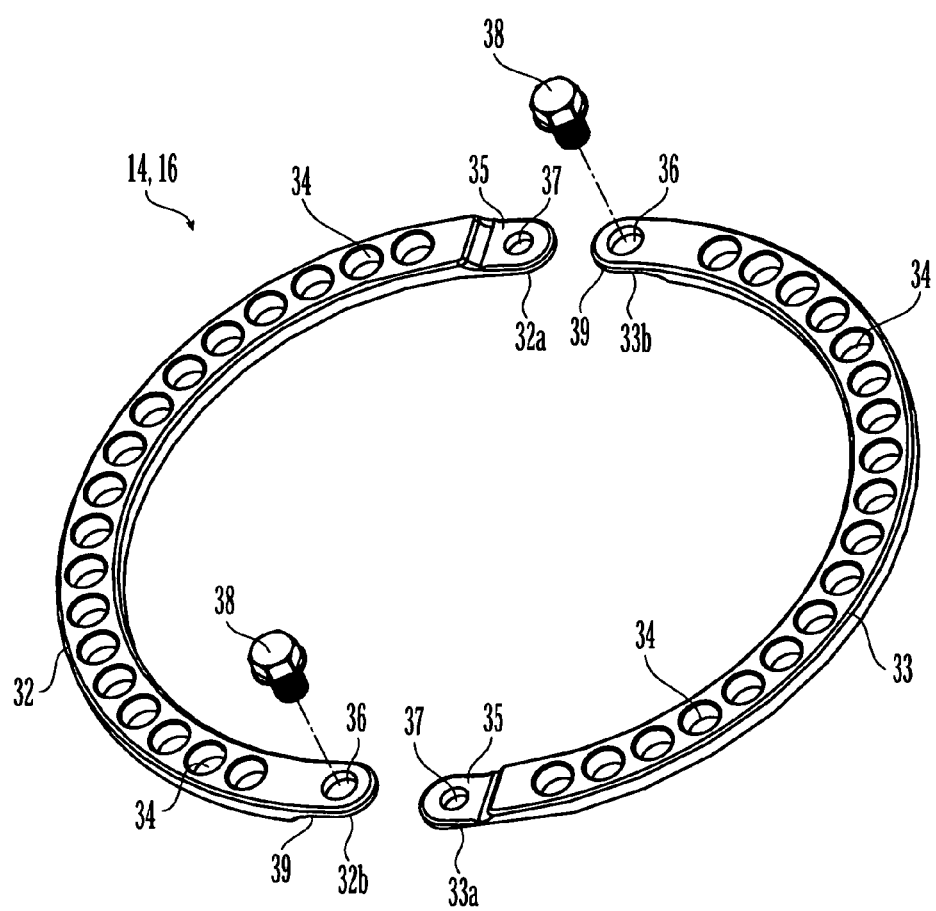
FIG. 2 is an exploded perspective view of an exemplary embodiment of a ring assembly of the device of FIG. 1.

FIG. 2 illustrates that each ring assembly 14, 16 may be made of two or more ring segments 32, 33. Those skilled in the art will appreciate that the ring assemblies 14, 16 may be made of a single piece of material. A ring assembly 14, 16 may be sized and configured to be positioned entirely around a bone to form an external fixation system. It should be noted, however, that individual rings segments 32, 33 may be used to construct an external fixation system such that the external fixation device may only partially surround a bone. For example, an external fixation system may have an upper portion which may only have a single ring segment 32, which may only partially surround a bone, and a lower portion which may be a complete ring assembly 14, 16, to surround the entire bone. In other embodiments, an external fixation system may have upper and lower portions which may each comprise only a single ring segment 32, 33 such the entire external fixation system only partially surrounds a bone.

Ring assemblies 14, 16 may be made of any suitable material such as metal (e.g., stainless steel, titanium, aluminum, an alloy of two or more metals), plastic (e.g., high strength polymers), rubber, ceramic (e.g., carbon fiber, graphite) or a composite material (i.e., made up of two or more materials). Various factors may be considered when determining the material used to make the ring assemblies 14, 16, including but not limited to, for example, ability to withstand sterilization, ability to withstand forces exerted thereon, weight, durability, the ability to grip the ring assemblies 14, 16, particularly with latex gloves and its radiotransparency or radiotranslucent properties. The ring assemblies 14, 16 may be radiolucent or radioopaque. In embodiments where the ring assemblies 14, 16 may be radiolucent, radio-opaque markers (not shown) may be incorporated into or attached to the ring assemblies 14, 16. The radio-opaque markers may assist a surgeon in properly aligning the ring assemblies 14, 16 relative to a patient's anatomy.

Ring segments 32, 33 may be substantially identical to each other and may include means for securing the ring segments to each other. In one embodiment, ring segment 32 may have ends 32a, 32b which may form flanges 35, 39, respectively, and the ring segment 33 may have ends 33a, 33b which may form flanges 35, 39, respectively. The flanges 35, 39 of ring segment 32 may be connected to the flanges 39, 35, respectively, of ring segment 33. The flanges may have a thickness which may be less than the thickness of the rest of the ring segments 32, 33 (e.g., one half the thickness of the rest of a ring segment 32, 33). In this way, when the flanges 35, 39 of the rings segments engage each other, the flanges 35, 39 may have a combined thickness which may be substantially the same as the thickness of the rest of the ring segments 32, 33. Such a construction may result in the upper surface 14a, 16a and lower surface 14b, 16b of the ring assemblies 14, 16 forming planes.

The ring segments 32, 33 may be engaged to each other in various ways. In one embodiment, for example, flanges 35, 39 may have openings 37, 36, respectively, which may align with each other when the ends 32b, 33a and 32a, 33b engage each other. Such a construction may enable a fastening device (e.g., screw or bolt) to be inserted through the openings 36, 37 and secure the segments 32, 33 to each other. In one embodiment, at least one hole 36, 37 may be threaded such that a threaded screw or bolt 38 may pass through the unthreaded hole 36, 37 and threaded into a threaded hole 36, 37. Alternatively, one or both holes 36, 37 may be unthreaded and a nut (not shown) may be secured to the screw or bolt 38 such the a portion of the ring segment 32, 33 may be held between the nut and the head of the screw or bolt 38. It should be understood by those skilled in the art that any means for engaging ring segments 32, 33 is envisioned.

Furthermore, ring assemblies 14, 16 may have a plurality of openings 34 therethrough which may provide connection points for clamps, distractors/compressors, and other components. The openings 34 may be threaded or unthreaded, and may be sized and configured to receive and support clamps, distractors/compressors, or other components by various removable or non-removable connection means including, for example, screws, bolts, nuts, clamps, welds, rivets, or any other suitable attachment means. The configuration of the ring assemblies 14, 16, in conjunction with one or more linear distractors 18 or other components, may provide an external fixation frame for attaching and supporting clamps (e.g., clamp 200, FIG. 11) or other components (e.g., rods, bars and bone pins, screws and/or wires) for fixation of bone segments.

In an embodiment where the ring segments 32, 33 and/or ring assemblies 14, 16 may be made of carbon fiber or graphite, a mat or sheet of carbon fiber or graphite may be rolled and/or folded and may be inserted into a mold. A resin or epoxy may be inserted into the mold so that the resin/epoxy permeates the mat/sheet, and the mat/sheet and resin/epoxy may be compressed to form the ring segments 32, 33 and/or an entire ring assemblies 14, 16. Thereafter, the ring segments 32, 33 and/or ring assemblies 14, 16 may be machined to form, for example, openings 34 therethrough and/or to create various features (e.g., flanges 35, 39 and holes 36, 37). Those skilled in the art will appreciate that carbon fiber or graphite ring segments/ring assemblies may be formed by any other method known in the art.

Figure 3A:
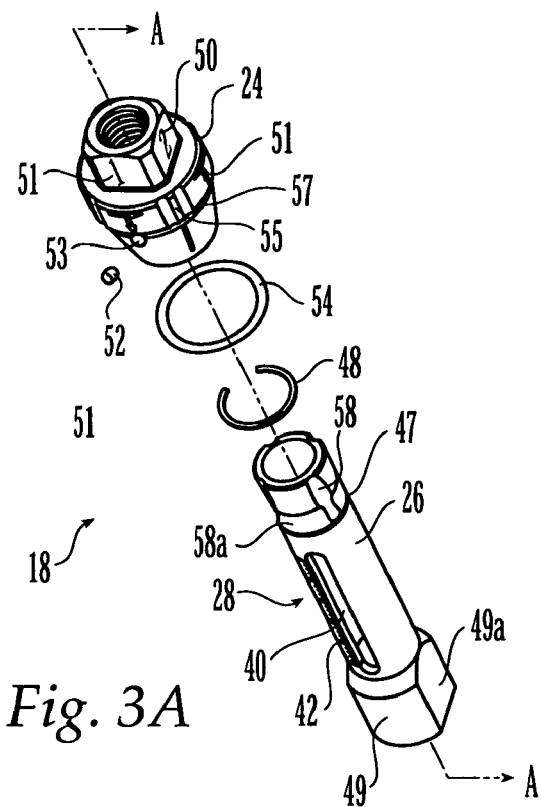
FIG. 3A is an exploded perspective view of an exemplary embodiment of a linear distractor assembly of the device of FIG. 1.
Figure 3B:
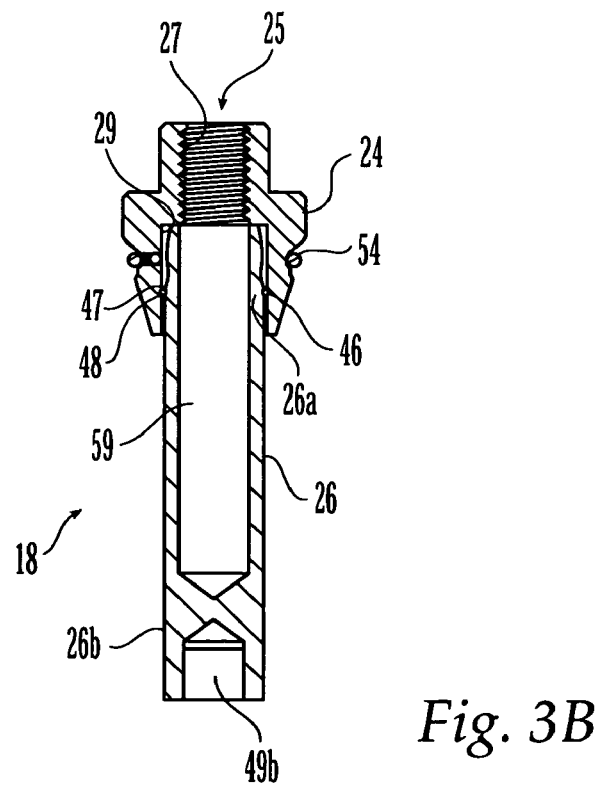
FIG. 3B is a cross-sectional view of the linear distractor assembly of FIG. 3A along line A-A.

As shown in FIG. 1, the linear distractors 18 may be attached to and in between the ring assemblies 14, 16 so that the distractors 18 may be substantially parallel with respect to each other as shown, or the distractors may also be oriented at non-parallel angles. The axis 18a of the distractors 18 may also be at an angle (e.g., perpendicular) with respect to the ring assemblies 14, 16. Moreover, as shown in FIGS. 1, 3A and 3B, the linear distractor 18 may have a body portion 26, an adjustment knob 24 which may be operably associated with the body portion 26, and an elongated member (e.g., threaded rod 20) which may engage the knob 24.

The components of the linear distractor 18 may be made of any suitable material such as metal (e.g., stainless steel, titanium, aluminum, an alloy of two or more metals), plastic, rubber, ceramic or a composite material (e.g., carbon fiber, graphite) or made up of two or more materials. Various factors may be considered when determining the material used to make the components of the distractor 18, including but not limited to, for example, ability to withstand sterilization, ability to withstand forces exerted thereon, weight, durability, and the ability to grip the components, particularly with latex gloves. The components of the distractor 18 may be radiolucent or radioopaque. In embodiments where the components may be radiolucent, radio-opaque markers (not shown) may be incorporated into or attached to the components.

The body portion 26 may be any shape such as, for example, cylindrical. The body portion 26 may have a distal end 26a which may be operably associated with the knob 24 and a proximal end 26b which may be attached to the second ring assembly 16. The proximal end 26b of the body portion 26 may have an enlarged portion 49, which may have one or more engagement portions (e.g., flat surface 49a and/or a knurled surface) to assist in tightening the body portion 26 to and/or loosening the body portion 26 from the ring assembly 16. The body portion 26 may have an inner passage 59 which may have a dimension which is larger than the diameter of the threaded rod 20 so that threaded rod 20 may be moved therein. The body portion 26 may also have a gauge 28 for measuring and displaying changes in position of the thread rod 20 within the inner cavity 59. The gauge 28 may include an elongated window 40 which may extend along the axis 18a so that an operator may visualize the position of the proximal most end 20b of the rod 20 relative to the gauge 28. In particular, the gauge 28 may have a scale or markings 42 along window 40 for measuring the position of the proximal most end 20b of the rod 20. In this way, an operator may be able to determine the amount of distraction and/or reduction/compression applied by the system 10. In other embodiments, the threaded rod 20 may have one or more calibration markings (not shown) which may be visible through window 40.

In one embodiment, the markings 42 may be applied to or positioned on body portion 26 after setting an initial position of rod 20 within window 40, such that changes in position of rod 20 may be measured from the initial position (e.g., "0"). For example, markings 42 may be printed on a sticker or other medium that may be applied to body portion 26 after initial assembly and set-up of external fixation system 10. The markings 42 may correspond to calibrated units of measure (e.g., millimeters, centimeters, inches, or fractions thereof) or the markings 42 may correspond to a particular distraction protocol to be followed (e.g., showing lines where the proximal end 20b of the rod should be aligned).

In one preferred embodiment, the knob 24 may be rotatably coupled to body portion 26. The knob 24 may include an inner bore 25, which may have a threaded portion 27 and an unthreaded portion 29. Threaded portion 27 may be sized and configured to receive the external threads on threaded rod 20. Unthreaded portion 29 of bore 25 may have a larger diameter than threaded portion 27 and may be dimensioned to fit over the distal end 26a of body portion 26.

In order to enable the knob 24 to move rotationally relative to the body portion 26 while preventing the knob 24 from moving axially along the axis 18a, a coupling 48 may be positioned between the knob 24 and the body portion 26. The coupling 48 may be made of, for example, steel, metal alloy, carbon fiber, plastic, rubber, ceramic or other material. The coupling 48 may be "C" shaped or may be a complete circle and may be positioned in an annular groove 46 in the knob 24 and/or a groove 47 in the body portion 26. Coupling 48 with a break or opening along a portion thereof such as with a "C" shaped coupling 48 may result in the coupling 48 being flexible, thereby facilitating placement or snap-fitting of the coupling 48 within the annular groove 46. With the C-ring coupling 48 fitted in groove 47, the knob 24 may be snap-fit over the end 26a of the body portion 26 so that the exterior surface of the coupling 48 may fit into groove 46 on the knob 24 to hold the knob 24 so that the knob 24 does not move axially on the body portion 26, but may rotate with respect to the body portion 26. An annular groove 58a in the body portion 26 may also prevent the knob 24 from being moved axially with respect to the body portion 26, while at the same time allowing rotational movement of the knob 24 relative to the body portion 26.

The threaded portion 27 of inner bore 25 of the knob 24 may be sized and configured to engage a proximal end 20b of threaded rod 20. Rotation of knob 24 in one direction (e.g., clockwise) may draw the threaded rod 20 into cavity 59 of body portion 26 and may thereby decrease the length of the linear distractor 18. Accordingly, the ring assemblies 14, 16 may move closer together, resulting in reduction or compression of a bone. Alternatively, rotation of knob 24 in the opposite direction (e.g., counterclockwise) may result in the threaded rod 20 moving out of the cavity 59 of the body portion 26 and may thereby increase the length of the linear distractor 18. Accordingly, the ring assemblies 14, 16 may move farther apart, resulting in distraction of a bone.

The knob 24 may be coupled to the body portion 26 in such a way that may allow for incremental movement of the knob 24 relative to the body portion 26 and, consequently, may result in incremental movement of the rod 20 and ring assemblies 14, 16. The knob 24 may have a radial passageway 53 which may receive an engaging device 52. The engaging device 52 may be moveable within the passageway or pin53. A biasing member 54, which may be ring shaped, may be positioned within an annular groove 57 in the knob 24. One example of biasing member 54 may be a rubber O-ring. The member 54 may be flexible and may bias the engaging device 52 into the bore 27 such that the engaging device 52 engages the body portion 24. In one embodiment, biasing member 54 may be unnecessary as the engaging device 52 may have a screw portion which engages threads (not shown) in the passageway 53. In one embodiment, biasing member 54 may be an elastic ring. In other embodiments, the biasing member 54 may be constructed of, for example, a metal, alloy, polymer or other composite material and may include a break or other feature that allows for some elastic expansion and/or contraction of biasing member 54.

As the knob 24 is turned, the engaging device 52 may move along the outside of the body portion 24. In one embodiment, the engaging device 52 may move along an annular groove 58a and may be snapped into the indentations 58 under the force of the biasing member 54. Such engagement of engaging device 52 and indentation 58 may result in mechanical stops wherein further rotation of knob 24 in the clockwise or counterclockwise direction requires additional force to move the engaging device 52 out of the indentation 58. This mechanical stop may be accompanied by an audible "click" or other sound that provides feedback to a user that the knob 24 has been moved a complete increment. The mechanical stop will also provide sensory or tactile feedback to a user.

This may facilitate controlled incremental adjustment of the linear distractor 18. The circumference around the knob 24 may dictate the distance between indentations 58 which, in turn, may dictate the amount of movement between the rings 14, 16 (i.e., there may be a proportional relationship between the amount the knob 24 is turned and the distance the rings 14, 16 move relative to each other) caused by a single incremental movement of the knob 24. For example, rotation of the knob 24 one click/increment may move the rings 14, 16 about 0.25 mm closer or farther apart. One skilled in the art will appreciate that other engaging devices and/or incremental adjustment mechanisms may be employed to provide such mechanical and auditory feedback to a user during adjustment.

The indentation 58 may be positioned at various increments around the knob 24. For example, indentations 58 may be positioned every 90 degree around the outside of the knob 24 (i.e., four indentations 58 in the knob 24). Alternatively, the indentations 58 may be positioned every 180 degrees around the knob 24 (i.e., two indentations 58 in the knob 24). In other embodiments, the indentations 58 may be positioned around the knob 24 with different amounts of space between two or more grooves (e.g., 45 degrees between two indentations 58 and 180 degrees between two indentations 58). The knob 24 may also include markings 51 and/or other features which may further assist in controlled and incremental adjustment of linear distractor 18. For example, the markings 51 may include numbers, arrows, or other marks or symbols which may be placed in known positions on the knob 24. In one embodiment, shown in FIG. 3A, the markings 51 may be numbers (e.g., "1", "2", "3" and "4") which may be positioned on surfaces 50 of the knob 24. The marking 51 may be substantially equally spaced around knob 24, such that each number may correspond to one-quarter turn of knob 24. While knob 24 is illustrated with four surfaces 50, the knob 24 may have any number of surfaces 50, for example, one surface (e.g., the surface may be circular) to ten or more surfaces 50, with or without markings 51. The construction of the knob 24 may depend upon the desired use and/or adjustment protocol. The number and positioning of the markings 51 may correspond to the number and positioning of the indentations 58 or other mechanical stops. Other symbols, such as arrow markings 51, may be used instead of or in conjunction with numbers, and may correspond to a indentation 58 or may be aligned with, for example, a reference mark (not shown) on body portion 26 to aid in precise adjustment to each desired increment. Each increment designated by the markings 51 and/or indentations 58 may correspond to a known change in length of linear distractor 18.

In an embodiment where the surfaces 50 may be substantially planar surfaces, the surfaces 50 may facilitate engagement by a wrench or other tool for rotation of the knob and/or adjustment of distractor 18. For example, knob 24 may include four flat surfaces arranged substantially perpendicular to each other around knob 24. Moreover, the knob 24 may also include ribs 55 or other features which may facilitate gripping and rotation of knob 24 by a user's hand or a tool. In some embodiments, at least a portion of the outer surface of the knob 24 may be textured (e.g., knurled).

The linear distractor 17 may be positioned between a pair of ring assemblies (e.g., ring assemblies 14, 16). The thread rod 20 may have a distal end 20a and a proximal end 20b. The distal end 20a of threaded rod 20 may be positioned through the openings 34 in the first ring assembly 14 and secured thereto by, for example, a pair of nuts 21, 22 which may be positioned on either side of the ring assembly 14. Other means of securing the rod 20 to the ring assembly 23 are also envisioned (e.g., bolts, screws, clamps, rivets, welds). The threaded rod 20 may be secured to the ring assembly 14 in a manner such that the rod 20 will not rotate during operation of the knob 24. The proximal end 20b of threaded rod 20 may be operably connected to the knob 24. For example, the threaded rod 20 may be rotatably coupled to threads 27 within knob 24 such that rotation of the knob 24 may results in the movement (e.g., linear movement along the axis 18a) of the knob 24 and/or the inner cavity 59 of the body portion 26 over the rod 20. The proximal end 26b of body portion 26 may have a recess 49b, which may be threaded, for receiving a fastening device (e.g., a screw 23 of FIG. 1) therein. Other means of securing the body portion 26 to the ring assembly 16 are also envisioned (e.g., bolts, screws, clamps, rivets, welds). The body portion 26 may be secured to the ring assembly 16 such that body portion 26 will not rotate with respect to ring assembly 16 during operation of knob 24. With the rod 20 and body portion 26 rotationally fixed with respect to the ring assemblies 14, 16, respectively, rotation of the knob 24 may result in axial movement of the rod 20 relative to the body portion 26 along the axis 18a and, thus, may result in axial movement of the ring assemblies 14, 16 with respect to each other. Furthermore, one skilled in the art will appreciate that, while the embodiment shown in FIG. 1 may include three distractors 18, other embodiments may include two, four or more distractors 18 depending upon the desired application.

Fasteners which may have selectively engageable features, such as, for example, nut 60 (FIGS. 4A-4E) and tightening member 72 (FIGS. 6A-6C), may be incorporated into external fixation devices and/or distraction/reduction/compression assemblies. For example, in the external fixation device 10, such selectively engageable fasteners may be employed instead of or in addition to traditional fasteners (e.g., nuts 21, 22; bolt 23) to attach a threaded rod 20 to ring assembly 14 or the body portion 26 to ring assembly 16. In one embodiment, the knob 24 of linear distractor 18 may be configured to include selectively engageable features similar to the nut 60 and/or tightening member 72 to allow rapid assembly, removal and/or adjustment of, for example, the rod 20.

Figure 4A:
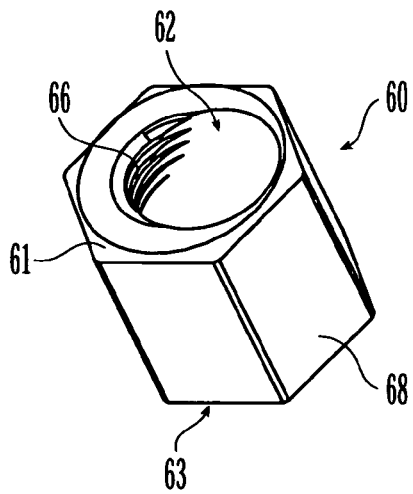
FIG. 4A is a perspective view of an exemplary embodiment of a tightening member.
Figure 4B:
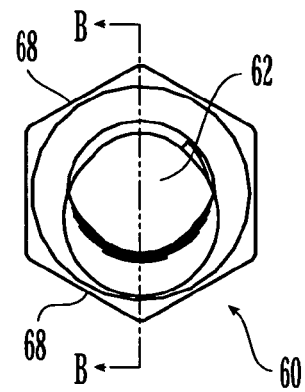
FIG. 4B is an end view of the tightening member of FIG. 4A.
Figure 4C:
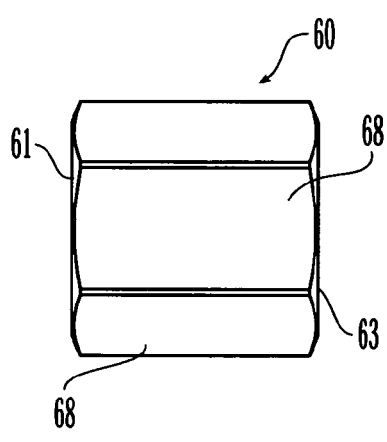
FIG. 4C is a side view of the tightening member of FIG. 4A.
Figure 4D:
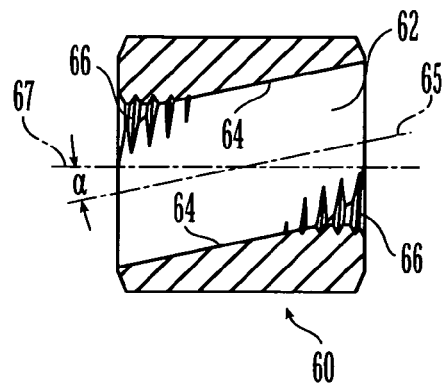
FIG. 4D is a cross-sectional view of the tightening member of FIG. 4A along line B-B.

FIGS. 4A through 4E illustrates a fastener which may be used to connect the linear distractor 18 and/or other components of an external fixation system to a ring assembly 14, 16. The tightening member may be a selectively engageable nut 60 and may have an axis 67. The nut 60 may have a bore 62 forming a passage from one end 61 of the nut 60 to the other end 63 of the nut 60. The bore 62 may have an axis 65 which may be substantially oblique with respect to the axis 67 and/or the ends 61, 63. Axis 65 may be at an angle α with respect to axis 67 of, for example, between about 8 degrees and about 16 degrees, more preferably, between about 10 degrees and about 14 degrees and, most preferably, between about 11 degrees and about 13 degrees. The ends 61, 63 may be oriented substantially parallel to each other and may be perpendicular to the sides 68 of nut 60. As shown in FIG. 4D, the bore 62 may have an unthreaded portion 64 and threaded portions 66. The threaded portions 66 may be adjacent to each end 61, 63 and may be opposite or diametrically opposed to each other. Each threaded portion 66 may cover less than half of the circumference of bore 62 and may extend a distance into the bore 62 from each end 61, 63. Such a configuration may be especially useful when an operator desires to, for example, connect a rod 20 to ring assembly 14, to secure body portion 26 to ring assembly 16, to attach clamps, bone connection elements (e.g., pins, screws or wires) to ring assemblies 14, 16, or anywhere else on device 10 where rapid assembly and adjustability may be desired.

Figure 5A:
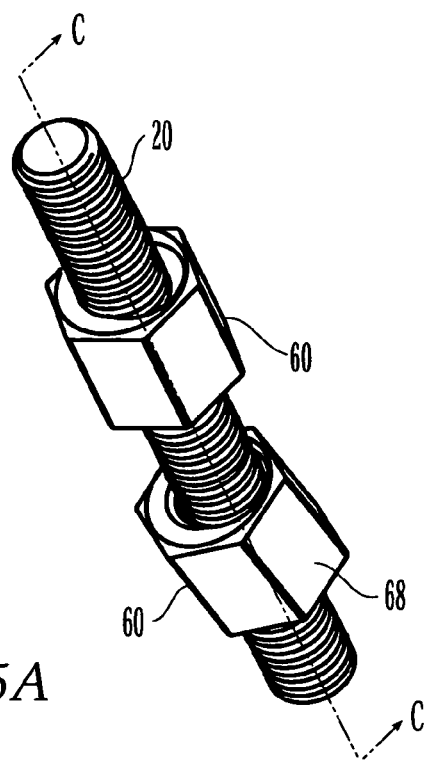
FIG. 5A is a perspective view of an exemplary embodiment of an assembly with the tightening member of FIG. 4A in various positions on an elongated member.
Figure 5B:
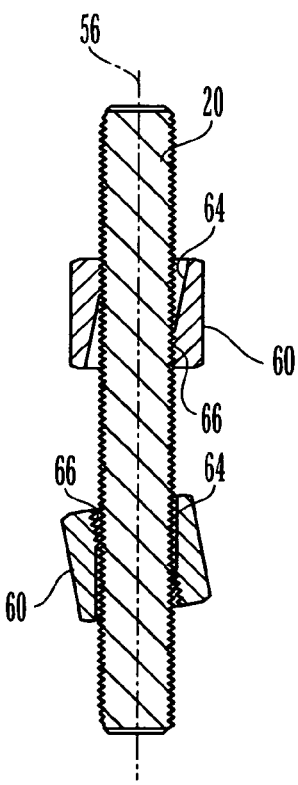
FIG. 5B is a cross-sectional view of the assembly of FIG. 5A along line C-C.

FIGS. 5A and 5B illustrates the nut 60 positioned on a rod 20. When the nut 60 is positioned such that the axis 65 of the bore 62 is aligned with the axis 56 of a rod 20, the nut 60 may be moved freely up and down the rod 20. Such a construction may eliminate the need to thread the nut 60 along the entire length of the rod 20 or other elongated member. When the nut is positioned such the that axis 67 of the nut 60 is aligned with the axis 56 of the rod 20, the threaded portions 66 of the nut 60 may engage the threads of the rod 20 such that the nut 60 may be threaded up and down the rod 60 (i.e., rotated so that nut 60 may move up and down threaded rod 60). The nut 60 may be rotated on the rod 20 to tighten and secure ends 61, 63 against a desired object (e.g., ring 14 or 16). The nut 60 may be loosened and disengaged from thread rod 20 by rotating the nut 60 so that the ends 61, 63 are not positioned against an object (e.g., ring 14, 16). The nut 60 may then be tilted such that the axis 65 of the bore 62 may be aligned with the axis 56 of the rod 20, and then the nut 60 may be moved swiftly, without rotation, up and down along the length of the rod 20.

Figure 4E:
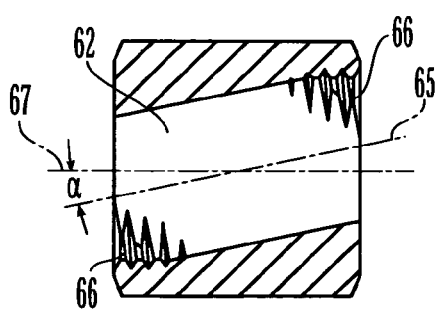
FIG. 4E is a cross-sectional view of an exemplary embodiment of an alternative tightening member.

In an alternative embodiment of nut 60 as illustrated in FIG. 4E, the relative configurations of unthreaded 64 portion and threaded 66 portion of bore 62 may be reversed. In this way, when the nut is positioned such that axis 67 of the nut 60 is aligned with the axis 56 of the rod 20, the nut 60 may be moved freely up and down the rod 20. When the nut 60 is positioned such that the axis 65 of the bore 62 is aligned with the axis 56 of a rod 20, the threaded portions 66 of the nut 60 may engage the threads of the rod 20 such that the nut 60 may be threaded up and down the rod 60. Such a configuration may be used in an external fixation device such as device 10, for example, to secure a rod 20 at an angle with respect to one or more ring assemblies 14, 16, or to secure other objects at oblique angles relative to each other.

Figure 6A:
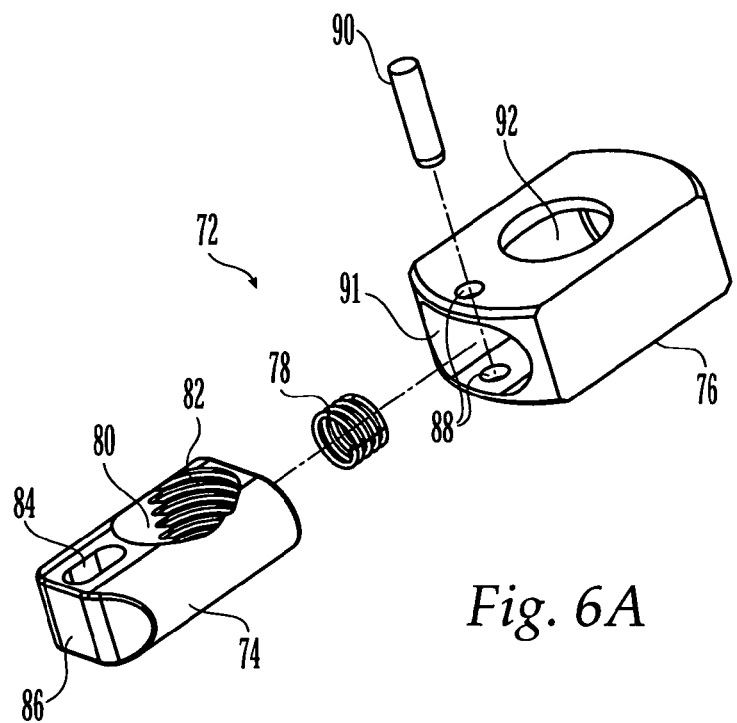
FIG. 6A is an exploded perspective view of exemplary embodiment of alternative tightening member.
Figure 6B:
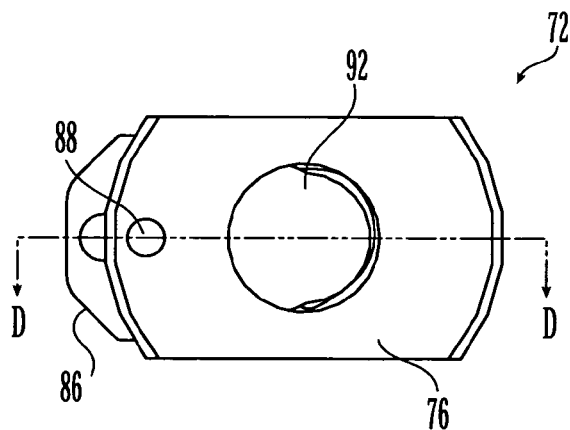
FIG. 6B is a top view of the tightening member of FIG. 6A.
Figure 6C:
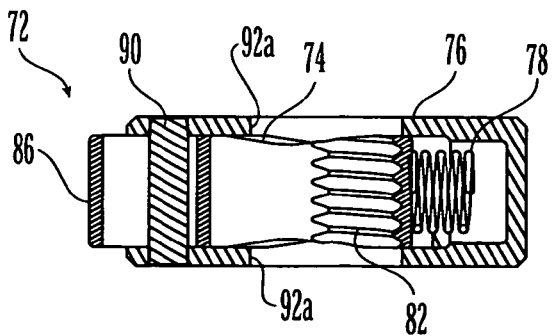
FIG. 6C is a cross-sectional view of the tightening member of FIG. 6A along line D-D.

FIGS. 6A through 6C illustrates an alternative embodiment of a tightening member. The selectively engageable tightening member 72 may have a housing 76, a lateral opening 91 through the housing 76 and an inner body 74 positioned within the lateral opening 91 of the housing 76. A biasing member 78 may be positioned between an inner surface of the housing 76 and the inner body 74 such that biasing member 78 may bias the inner body 74 out of the housing 76 (i.e., towards lateral opening 91). In this way, the end 86 of inner body 74 may extend out of the housing 76. The inner body 74 may have a partially threaded bore 80 and an elongated opening 84. The threading is preferably along about 180 degrees of the bore 80. A pin 90 may be inserted through holes 88 of the housing 76 and elongated opening 84 of the inner body 74 so that the inner body 74 may be held within the housing 76. The pin 90 is preferably fixed in holes 88, but may be removable for sterilization or other purposes. The inner body 74 may be moved in and out of the housing by an operator depressing/pushing and releasing surface 86 of the inner body 74. The pin 90 may slide in the elongated opening 84 as the inner body 74 is moved in the housing 76.

The housing 76 may also include an aperture 92 passing through the housing 76. The aperture 92 may be sized and configured to be aligned with bore 80. An elongated member (e.g., threaded rod 20) may be positioned through the aperture 92 and bore 80. When body 74 is released or not depressed, biasing member 78 may bias an end of the elongated opening 84 against the pin 90 and the threaded portion 82 of bore 80 may engage the threaded rod 20. The rod 20 may be held between the wall 92a of the aperture 92 and the threaded portion 82 of the bore 80. In this position, the tightening member 72 may be rotated relative to the rod 20 to move the member 72 relative to the rod 20. When the inner body 74 is depressed into the housing 76 against the force of the biasing member 78, the tightening member 72 may move freely on the elongated member as the threaded portion 82 in the bore 80 is released from the threads on the rod 20. Similar to the nut 60, the construction of the tightening member 72 may allow for quick and coarse movement of tightening member 72 relative to the threaded rod 20. One skilled in the art will appreciate that the tightening member 72 and/or nut 60 may include alternative or different features for providing selective engagement of an elongated member without departing from the scope of the present invention.

Figure 7A:
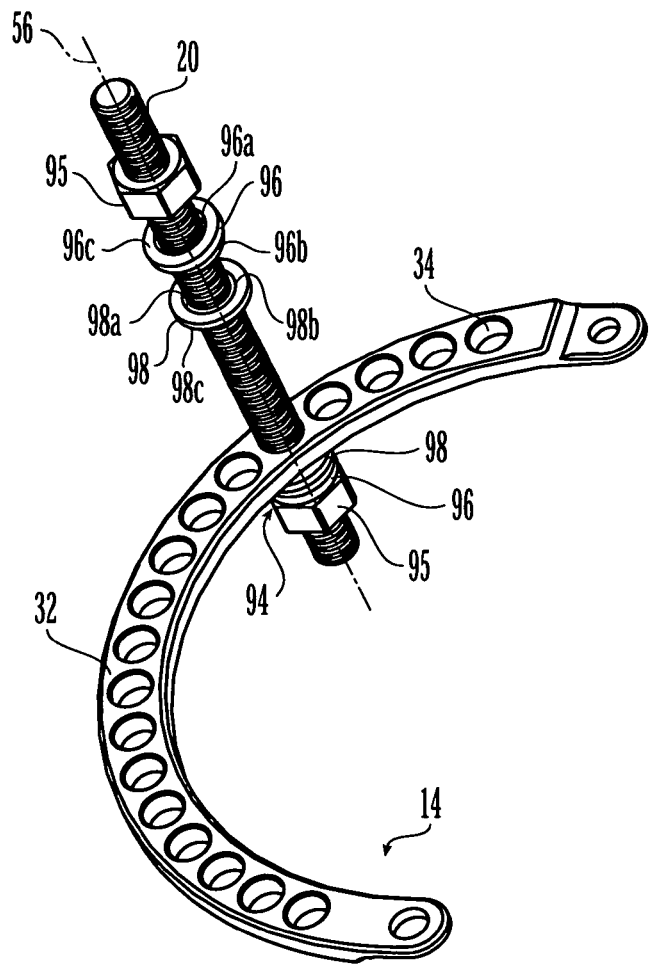
FIG. 7A is a perspective view of an exemplary embodiment of angulation washers attached to an exemplary ring assembly.
Figure 7B:
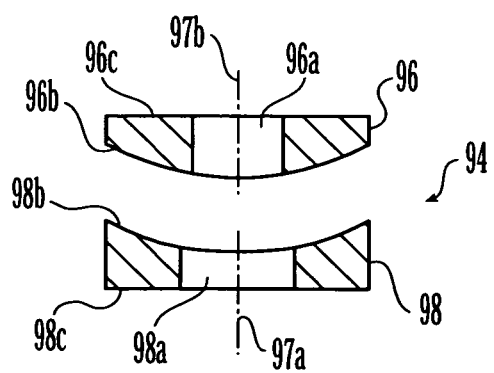
FIG. 7B is a cross-sectional view of the washers of FIG. 7A.

In order to enable angulation of two or more components of an external fixation system relative to each other (e.g., positioning rod 20 at an angle with respect to ring assembly 14, ring segment 32, 33), an external fixation system may incorporate an angulation washer assembly 94 as illustrated in FIGS. 7A and 7B. The angulation washer assembly 94 may include a male washer 96 and a female washer 98. The male washer may be shaped as an annular disc and may have a central hole or passage 96a therethrough. Male washer 96 may also have a convex portion 96b on a first side of washer 96, and a substantially planar surface 96c on a second, opposite side of the washer 96. Similar to the male washer 96, the female washer 98 may be configured as an annular ring with a central hole or passage 98a therethrough. Female washer 98 may also have a concave portion 98b on a first side of washer 98, and a substantially planar surface 98c on a second, opposite side of the washer 98. The concave portion 98b of the female washer 98 may be sized and configured to receive the convex portion 96b of the male washer 96 such that the male washer 96 and female washer 98 may move relative to each other.

The passage 96a, 98a of the male and female washers 96, 98, respectively, may be sized and configured to receive a component of an external fixation system such as, for example, rod 20. The passage 98a through the female washer 98 may be dimensioned such that the axis 56 of a rod 20 (or other component) placed therethrough may be positioned at an oblique angle with respect to axis 97a of the washer 98. The passage 96a through the male washer 96 may have a smaller dimension than the passage 98a of the female washer 98 such that the axis 56 of a rod 20 (or other component) placed therethrough may be coaxial with the axis 97b of the washer 96.

Figure 7C:
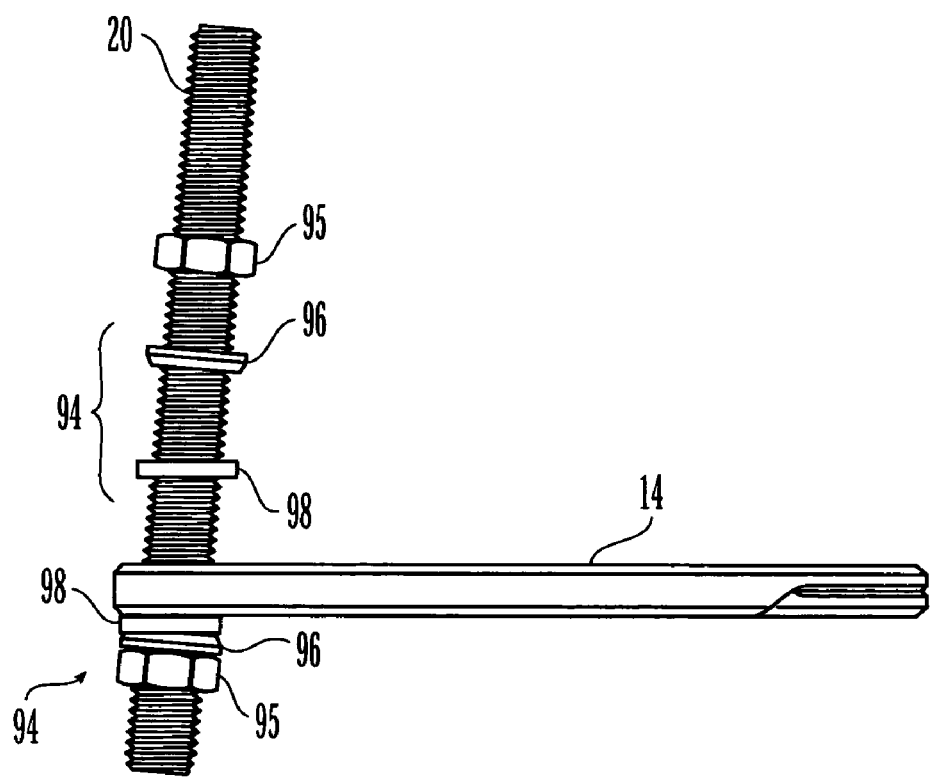
FIG. 7C is a side view of the assembly of FIG. 7A.

As shown in FIGS. 7A and 7C, the washers 96, 98 may be placed on the rod 20. The rod 20 may be positioned through an opening 34 in, for example, ring assembly 14 (i.e., ring segment 32, 33) or through an opening in another object secured to the rod 20. The female washer 98 may be positioned adjacent the ring assembly 14 so that the surface 98c may abut the ring assembly 14 and the concave portion 98b may face away from ring assembly 14. The convex portion 96b of male washer 96 may engage the concave portion 98b. A nut 95 or other fastening device (e.g., nut 60, tightening member 72) may engage the threads of the rod 20 such that washers 96, 98 may be located between nut 95 or other fastener and ring assembly 14. The surface 96c of the male washer 96 may engage a surface of the nut 95 or other fastener. The rod 20 may be oriented at an angle with respect to the ring assembly 14. As the nut 95 or other fastener is rotated, the male washer 96 may be urged against the female washer 98. In order to hold the rod 20 to the ring assembly 14, another washer assembly 94 and nut 95 (or nut 60, FIG. 4E) may be positioned on an opposite side of the ring assembly 14. Thus, the rod 20 may be held at an angle relative to the ring assembly 14. This angle may be adjusted by loosening one of nuts 95 or other fastening members, positioning the rod 20 at a desired angle, and re-tightening the nut 95 or other fastener member.

In alternative embodiments, features of nut 95 and male washer 96 may be combined (i.e., the nut 95 may have a convex portion which may engage the concave surface 98b of the female washer 98). In another embodiment, a nut may be unnecessary and one or more of male washers 95 may have a threads within the passage 96a for engaging threads of the rod 20. Those skilled in the art will appreciate that nut 60 of FIG. 4E may be used in place of a washer assembly 94 and nut 95 (e.g., the rod 20 may be positioned in a ring assembly 14 and may be held thereon by positioning one nut 60, shown in FIG. 4E, on either side of the ring assembly 14).

Figure 8:
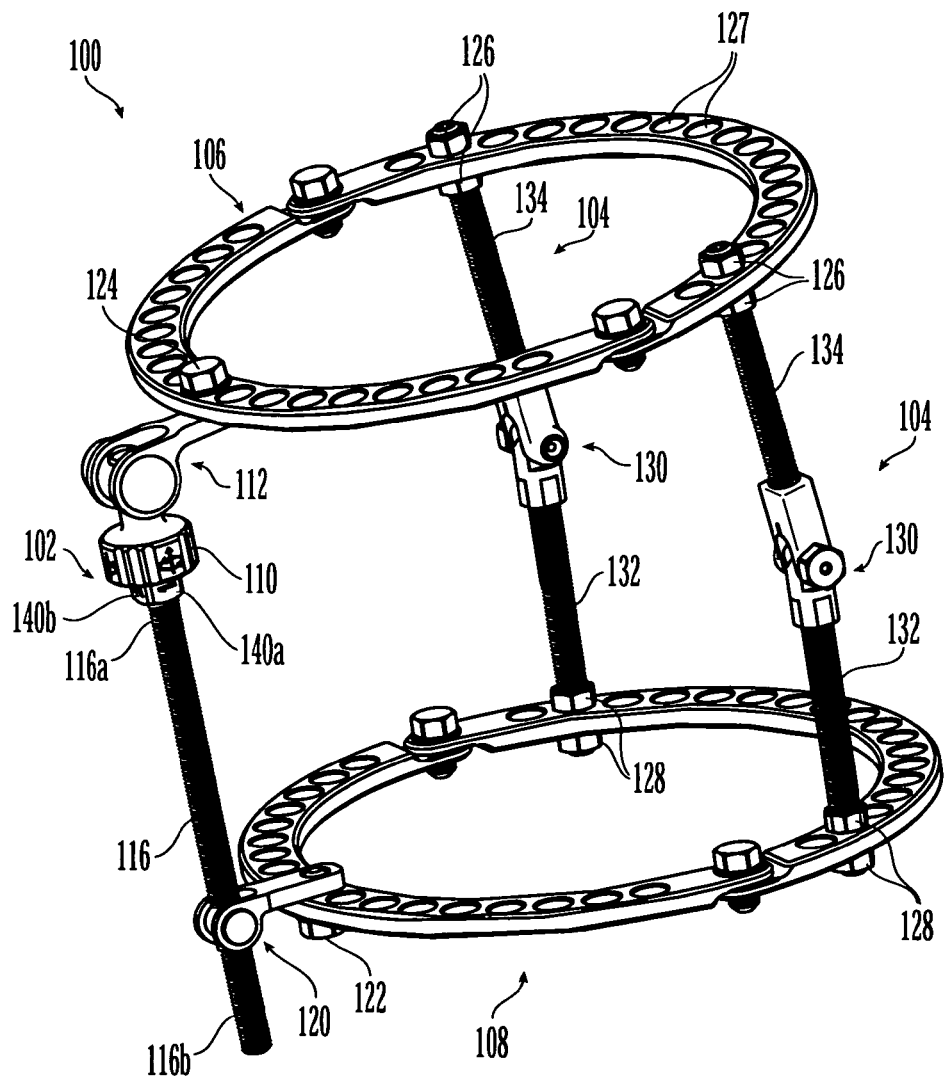
FIG. 8 is a perspective view of an alternative exemplary embodiment of an external fixation system.

In procedures where it may be desirable to angle the ring assemblies and/or segments (i.e., move portions of the ring assemblies towards or away from each other) with respect to each other, one or more angular distractors and/or angular separation assemblies may be used. Referring now to FIG. 8, an external fixation system 100 may include two or more ring assemblies 106, 108 separated by at least one angular distractor 102 and one or more angular separation assemblies 104. Ring assemblies 106, 108 may be similar to ring assemblies 14, 16 and segments 32, 33 as shown in FIGS. 1 and 2 and may have a plurality of openings 127 which provide connection points for clamps, bolts, rods and/or other connection assemblies for securing the bone connection elements (e.g., bone pins, screws and/or wires). The configuration of the ring assemblies 106, 108, in conjunction with one or more angular distractors 18 and/or angular separation assemblies 104 may provide an external fixation frame for attaching and supporting clamps (e.g., clamp 200, FIG. 11) or other components (e.g., rods, bars and bone pins, screws and/or wires) for fixation of bone segments.

Figures 9A, 9B:
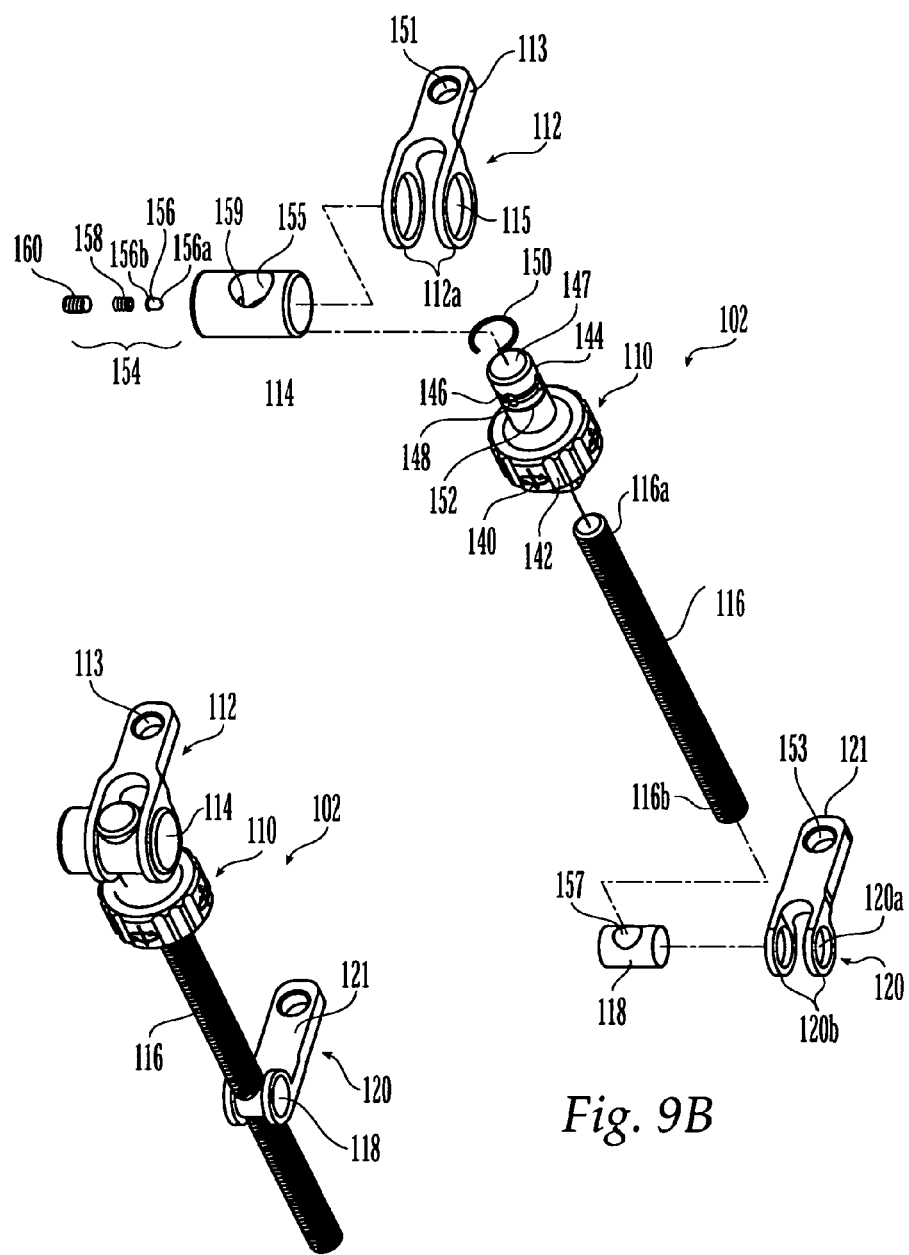
FIG. 9A is a perspective view of an exemplary embodiment of an angular distractor assembly of FIG. 8.
FIG. 9B is an exploded perspective view of the angular distractor assembly of FIG. 9A.

As shown in FIGS. 9A and 9B, the distractor assembly 102 may include an elongated member (e.g., a threaded rod 116), an adjustment knob 110 operably associated with the elongated member, a first connector 112 operably connected to the knob 110 and a second connector 120 operably connected to the elongated member. It should be noted that the components of the angular distractor 102 may be made up of the same materials as the linear distractor 18.

The threaded rod 116 may have a distal end 116a and a proximal end 116b. The distal end 116a of the rod 116 may be rotatably connected to the knob 110. As shown in FIG. 9B, the knob 110 may have a neck portion 144 and a bore 147 which may extend through the knob 110. The bore 147 may have an internal threaded portion (not shown) for engaging the threaded rod 116. In one embodiment, the neck portion 144 may be cylindrical and may be positioned within a bore 155 in barrel nut 114 of connector 112.

As shown in FIGS. 9A and 9B, the barrel nut 114 may be positioned through a passageway 115 in the connector 112 and may be rotatable relative to the connector 112. In particular, the barrel nut 114 may be positioned through extensions 112a of the connector 112, which may form loops defining the passageway 115, so that the barrel nut 114 may rotate within the passageway 115. The connector 112, in turn, may be attached to a ring assembly 106. Such a construction may result in the connector 112 acting as a hinge such that the rod 116 may be angled with respect to the ring 106. The connector 112 may have an extended portion 113 which may have an opening 151 for attaching the connector 112 to ring assembly 106 or another structure. In one embodiment, the opening 151 may be threaded to accept a fastener (e.g., screw 124), which may pass through and secure ring assembly 106 and connector 112. Alternatively, the opening 151 may be unthreaded and may be dimensioned to allow a bolt to pass through opening 151 and into a corresponding opening 127 in the ring assembly 106. The bolt may then be secured in place using a threaded nut or other fastener. Alternatively, clamps, welds, pins, rivets or other connection means may be used to secure the connector 112 to ring 106.

A coupling 150, which may be similar in structure and material to the coupling 48 of the linear distractor 18, may be positioned in a groove 152 in the neck portion 144 and a groove (not shown) in the barrel nut 114 so that the coupling 150 may be held between the neck portion 144 and the barrel nut 114. The coupling 150 may be "C" shaped or otherwise have a break along its length. Such a configuration may enable the coupling to be positioned on the knob 110 during assembly. The coupling 150 may allow the knob 110 to rotate relative to the barrel nut 114 while, at the same time, may prevent axial movement of the knob 110 relative to the barrel nut 114.

The knob 110 and barrel nut 114 may include corresponding structures for incremental adjustment and/or rotation of the knob 110. For example, the knob may have one or more receiving portions 148 and the barrel nut 114 may have a detent assembly 154 for engaging the receiving portions 148. The detent assembly 154 may be positioned in a passage 159 of the barrel nut 114 and may comprise an engaging portion 156, a biasing member 158 and a holding member 160 (e.g., a set screw). Alternatively, the detent assembly 154 may be a one-piece ball detent mechanism which may be attached to the barrel nut 114. In one embodiment the holding member 160 may be a plug 160 which may be threaded and dimensioned to engage and secure with threads (not shown) in the passage 159 of the barrel nut 114. Furthermore, the engaging portion 156 may be any shape, for example, ball or bullet shaped. The engaging portion 156 and barrel nut 114 may be configured such that the tip 156a of engaging portion 156 may extend into bore 155, while still captivating the engaging portion 156 within barrel nut 114. For example, the end of detent 156 opposite the tip 156a may include a lip or flange 156b which may be larger than the dimension at the end of the passage 159 proximate the bore 155. In one embodiment, the engaging portion 156 may move along an annular groove 146. The annular groove 146 may also function to keep the knob 110 and barrel nut 114 from moving axially with respect to each other.

The holding member 160 may hold the biasing member 158 and engaging portion 156 within the passage 159 such that the engaging portion 156 may be held between the knob 110 and the holding member 160. The biasing member 158 (e.g., spring) may bias the engaging portion 156 into the bore 155 so that the engaging portion 156 may engage the neck portion 144 of the knob 110. As the knob 110 is rotated relative to the barrel nut 114, the engaging portion 156 may move along the outer surface of the neck portion 144.

Upon rotation of the knob 110, the engaging portion 156 may move along an annular groove 146 and may be snapped into the receiving portion 148 under the force of the biasing member 158. Such engagement of engaging portion 156 and receiving portion 148 may result in mechanical stops wherein further rotation of knob 110 in the clockwise or counterclockwise direction requires additional force to move the engaging portion 156 out of the receiving portion 148. This mechanical stop may be accompanied by an audible "click" or other sound that provides feedback to a user that the knob 110 has been moved a complete increment. This may facilitate controlled incremental adjustment of the angular distractor 102. The circumference around the knob 110 may dictate the distance between receiving portions 148 which, in turn, may dictate the amount of movement between the rings 106, 108 (i.e., there may be a proportional relationship between the amount the knob 110 is turned and the distance the rings 106, 108 move relative to each other). One skilled in the art will appreciate that other engaging devices and/or incremental adjustment mechanisms may be employed to provide such mechanical and auditory feedback to a user during adjustment.

The receiving portion 148 may be positioned at various increments around the knob 110. For example, receiving portion 148 may be positioned every 90 degree around the outside of the knob 110 (i.e., four receiving portion 148 in the knob 110). Alternatively, the receiving portion 148 may be positioned every 180 degrees around the knob 110 (i.e., two receiving portion 148 in the knob 110). In other embodiments, the receiving portion 148 may be positioned around the knob 110 with different amounts of space between one or more receiving portions (e.g., 90 degrees between three receiving portions 148, and 180 degrees between two receiving portions 148).

The knob 110 also may also include markings 140, 140a and/or other features which may further assist in controlled and incremental adjustment of angular distractor 102. For example, the markings 140 may include numbers, arrows, or other marks or symbols which may be placed in known positions on the knob 120. In one embodiment, shown in FIG. 8, the markings 140a may be numbers (e.g., "1", "2", "3" and "4") which may be positioned on surfaces 140b of the knob 110. The marking 140, 140a may be substantially equally spaced around knob 110, such that each number may correspond to one-quarter turn of knob 110. In the embodiment shown in FIGS. 9A and 9B, marking 140 may be spaced 90 degrees apart around the circumference of knob 110, and positioned to correspond to receiving portions 148. Preferably, each increment designated by markings 140, 140a and/or by receiving portions 148 or other features that provide incremental mechanical stop positions, may correspond to a known change in respective angle or distance between ring assemblies 106, 108.

While knob 110 is illustrated with four surfaces 140b, the knob 110 may have any number of surfaces 140b, for example, one surface (e.g., the surface may be circular) to ten or more surfaces 140b, with our without markings 140, 140a. The construction of the knob 110 may depend upon the desired use and/or adjustment protocol. The number and positioning of the markings 140, 140a may correspond to the number and positioning of the receiving portions 148 or other mechanical stops. Other symbols, such as arrow markings 140, may be used instead of or in conjunction with numbers, and may correspond to receiving portions 148 to aid in precise adjustment to each desired increment. Each increment designated by the markings 140, 140a and/or receiving portions 148 may correspond to a known change in length of angular distractor 102.

In an embodiment where the surfaces 140b may be substantially planar surfaces, the surfaces 140b may facilitate engagement by a wrench or other tool for rotation of the knob and/or adjustment of distractor 102. For example, knob 110 may include four flat surfaces arranged substantially perpendicular to each other around knob 110. Moreover, the knob 110 may also include ribs 142 or other features which may facilitate gripping and rotation of knob 110 by a user's hand or a tool. In some embodiments, at least a portion of the outer surface of the knob 110 may be textured (e.g., knurled, grooves).

The proximal end 116b of the rod 116 may be coupled to a connector 120. As shown in FIGS. 9A and 9B, a barrel nut 118 may be positioned through a passageway 120a in the connector 120 and may be rotatable relative to the connector 120. In particular, the barrel nut 118 may be positioned through extensions 120b of the connector 120, which may form loops defining the passageway 120a, so that the barrel nut 118 may rotate within the passageway 120a. The connector 120, in turn, may be attached to a ring assembly 108. Such a construction may result in the connector 120 acting as a hinge such that the rod 116 may be angled with respect to the ring 108. The rod 116 may be positioned through a bore 157 in the barrel nut 118. The bore 157 may be threaded to engage the threads of the rod 116. The connector 120 may have an extended portion 121 which may have an opening 153 for attaching the connector 120 to ring assembly 108 or another structure. In one embodiment, the opening 153 may be threaded to accept a fastener (e.g., screw 122), which may pass through and secure ring assembly 108 and connector 120. Alternatively, the opening 153 may be unthreaded and may be dimensioned to allow a bolt to pass through opening 153 and into a corresponding opening 127 in the ring assembly 108. The bolt may then be secured in place using a threaded nut or other fastener. Alternatively, clamps, welds, pins, rivets or other connection means may be used to secure the connector 120 to rings 108.

In use, clockwise and/or counterclockwise rotation of the knob 110 of the angular distractor 102 may result in axial movement of the rod 116 through the knob 110 and, thus, may result in the rings 106, 108 moving towards (reduction/compression) or away (distraction) from each other.

Figure 10:
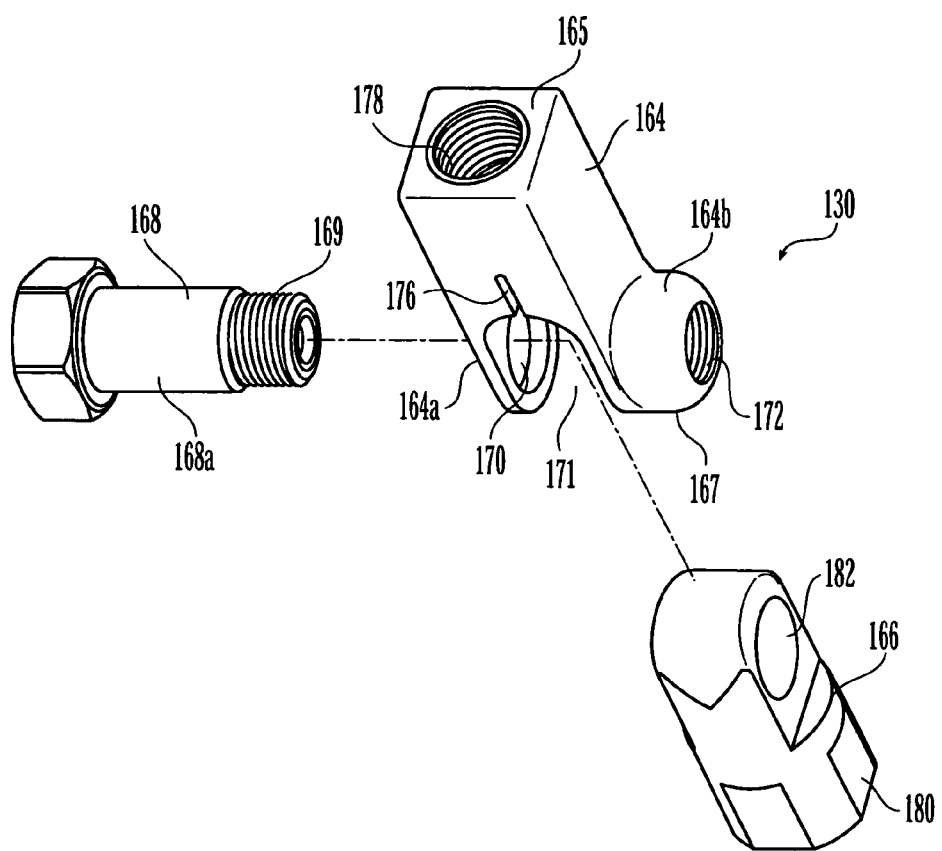
FIG. 10 is an exploded perspective view of an exemplary embodiment of a joint assembly of the system of FIG. 8.

In order to facilitate angular movement of rings 106, 108 relative to each other as well as hold the rings 106, 108 together, the external fixation system 100 may incorporate one or more connection assemblies 104. As illustrated in FIGS. 8 and 10, the connection assembly 104 may include a joint 130 having an upper body portion 164 and a lower body portion 166, a rod 132 connected between the lower body portion 166 and the ring 108 or other structure, and a rod 134 operably connected between the upper body portion 164 and the ring 106 or other structure. Rods 132 and 134 preferably have at least a portion that is threaded. In one embodiment, rods 132 and 134 may be unnecessary and the upper body portion 164 may be connected directly to the ring 106 and the lower body portion 166 may be connected directly to the ring 108. In other embodiments, only one rod 132, 134 may be necessary (e.g., the lower body portion 166 may be connected directed to the ring 108 and the upper body portion 164 may be connected to a rod 134 which, in turn, may be connected to the ring 106). The connection assembly 104 may be configured such that the joint 130 may move (i.e., the upper and lower body portions 164, 166 may rotate, pivot or angulate relative to each other) as the rings 106, 108 are moved towards and/or away from each other by the angular distractor 102. Moreover, the joint 130 may be configured so that the upper and lower body portions 164, 166 may be fixed with respect to each other once the rings 106, 108 are in a desired angular orientation with respect to each other.

The rod 134 may be attached to ring 106 using one or more nuts 126, which may be attached to rod 134 on either side of ring 106. Moreover, the rod 132 may be attached to the ring 108 using one or more nuts 128, which may be attached to the rod 132 on either side of the ring 108. One skilled in the art will appreciate that any other means for connecting rods 134, 132 and/or upper and lower body portions 164, 166 to rings 106, 108, respectively, is contemplated.

As shown in FIG. 10 the joint 130 may include an upper body portion 164, a lower body portion 166, and a connection member 168 (e.g., a bolt). One end 165 of upper body portion 164 may include a bore 178 for receiving an elongated member (e.g., rod 134 or bolt) or another means for attaching the joint 130 to the ring 106. Bore 178 may have threads and may be sized and configured to connect to the rod 134. The opposite end 167 of upper body portion 164 may have two extensions 164a, 164b, which may have an opening 171 therebetween for receiving a portion of the lower body portion 166. The extension 164a and 164b may have a hole or passage 170, 172, respectively, (threaded or unthreaded) which may be dimensioned to allow the connection member168 to pass therethrough. In one embodiment, the passage 170 may be unthreaded and the passage 172 may be threaded so as to receive a threaded portion 169 of the connection member 168. A notch 176 in the upper body portion 164 may allow for some lateral movement (flexibility) of extensions 164a, 164b during tightening of the connection member 168 such that the extensions 164a, 164b may move together as the connection member 168 is threaded into the passage 172. In an alternative embodiment, the passage 170 may be threaded and the passage 172 may be unthreaded and/or smooth. Alternatively, both passages 170, 172 may be threaded or both may be unthreaded and/or smooth. In an embodiment where one or both passages 170, 173 may be unthreaded and/or smooth, a connection member 168 such as a bolt may be passed through the extensions 164a, 164b and a nut may be tightened on the threaded portion 169 such that the extensions 164a, 164b may be positioned between the head of the bolt and the nut.

The lower body portion 166 may have a bore 182 and may be sized and configured so that at least a portion of the lower body portion 166 may be positioned between the two extensions 164a, 164b. The lower body portion 166 may be positioned between the extensions 164a, 164b such that the passages 170, 172 may be aligned with the bore 182. Such a configuration enables the connection member 168 to be passed through the passages 170, 172 and the bore 182, connecting the upper and lower body portions 164, 166 so that the portions 164, 166 may move (e.g., rotate) relative to each other. As shown in FIG. 10, this movement may be accomplished by positioning an unthreaded, relatively smooth portion 168a of the connection member 168 through the bore 182. It should be noted that the upper and lower body portions 164, 166 may be connected by a ball and socket configuration. For example, the lower body portion 166 may have a ball at one end which may be received in the opening 171 which may be in the shape of a socket for receiving the ball. Such a construction may allow for polyaxial movement of the upper and lower body portions 164, 166 relative to each other (i.e., the upper and lower body portions 164, 166 may rotate about multiple axes).

The connection member 168 may be tightened to the upper body portion 164 so that the upper and lower body portions 164, 166 may be held together but may move (e.g., rotate) relative to each other. In this way, as the rings 106, 108 are angled with respect to each other using the angular distractor 102, the upper and lower body portions 164, 166 may be angled relative to each other. Once the rings 106, 108 are at a desired angle with respect to each other, the connection member 168 may be fully tightened so the orientation of the body portions 164, 166 may be fixed relative to each other. To facilitate fixation of the body portions 164, 166, the notch 176 may allow the extensions 164a, 164b to flex towards each other so that the lower body portion 166 may be firmly held between the extensions 164a, 164b. In another embodiment, the body portions 164, 166 may be held together so that the body portions 164, 166 may always be rotatable with respect to each other. In this way, the body portions 164, 166 may move as the angular distractor 102 is moved incrementally by an operator and an operator is not required to tighten and loosen the connection member 168.

Lower body 166 also may include a bore (not shown) which may receive an elongated member (e.g., rod 132) and/or a fastener (e.g., bolt) to attach the lower body portion 166 to the ring 108. The bore may have threads for engaging threads of the rod 132 and/or fastener. In addition, lower body portion 166 may include surfaces 180, which may have a planar configuration, or other features to facilitate engagement by a wrench or other tool.

Figure 11:
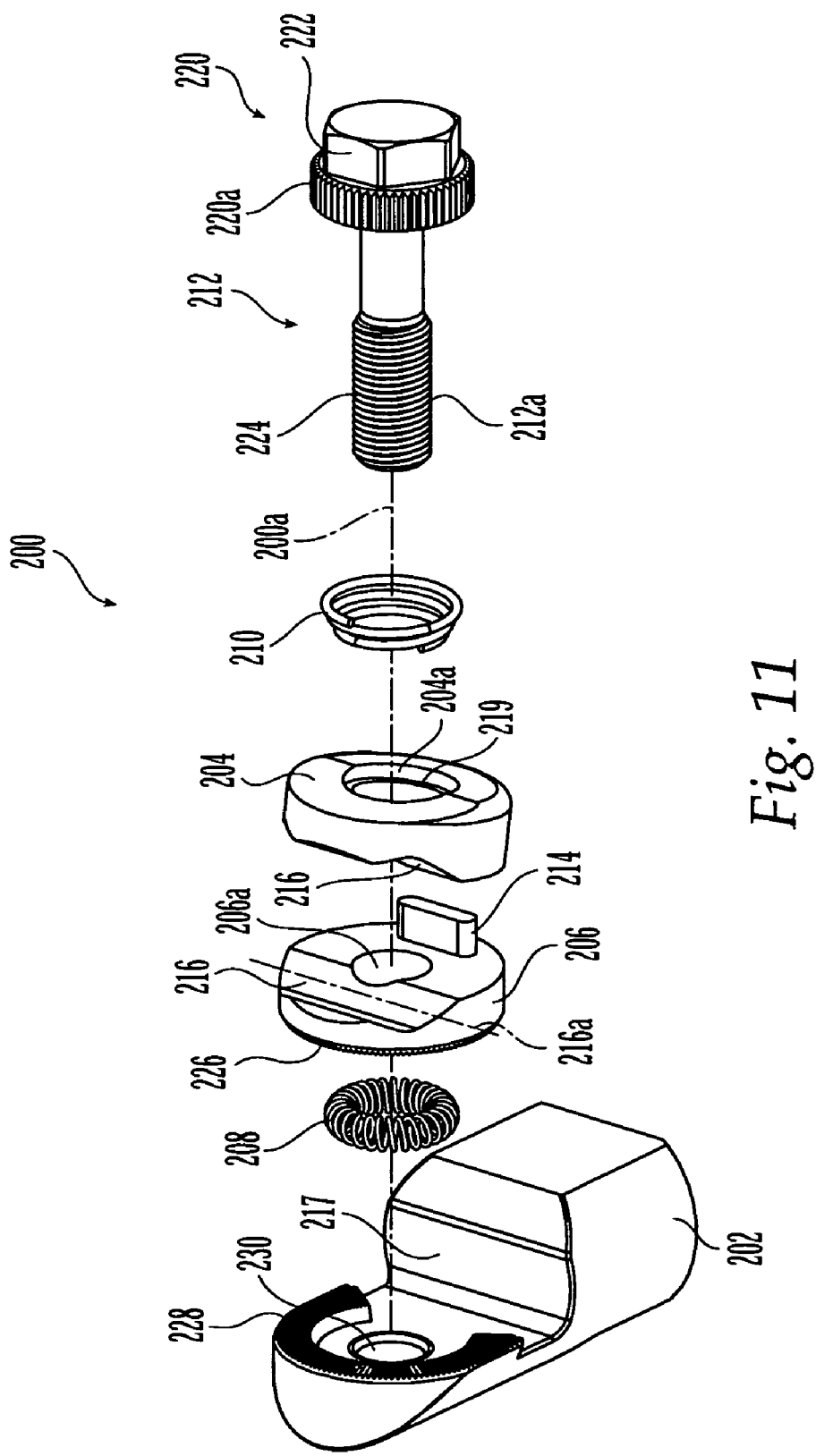
FIG. 11 is an exploded perspective view of an exemplary embodiment of a clamp assembly.
Figure 12:
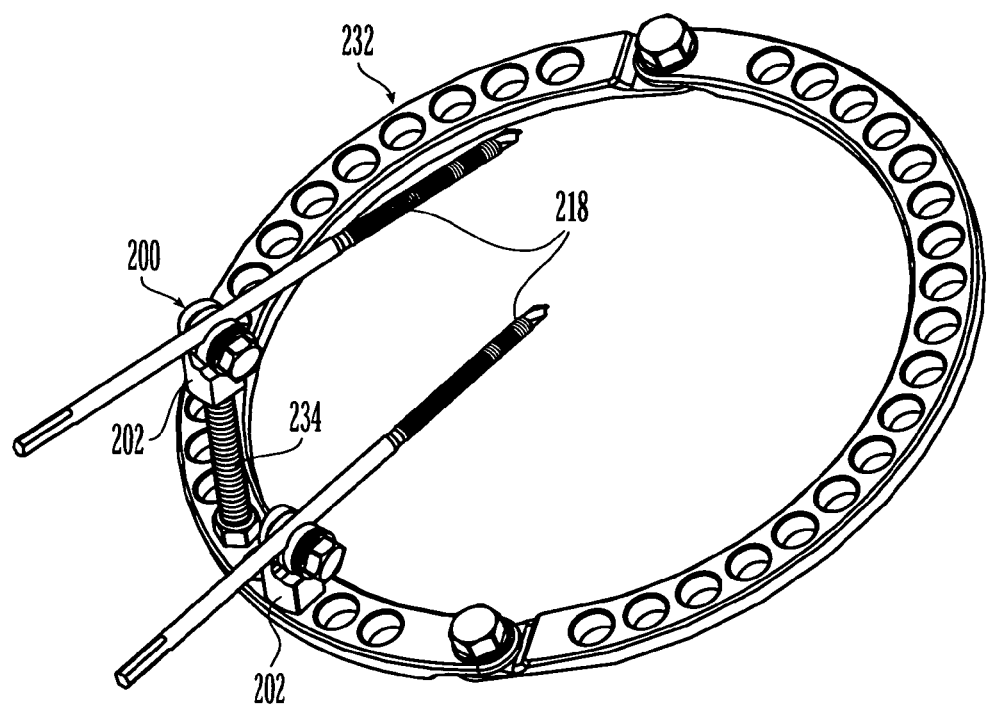
FIG. 12 is a perspective view of an exemplary embodiment of an assembly incorporating the clamp of FIG. 11.

Turning now to FIGS. 11 and 12, a clamp 200 may be incorporated into an external fixation system and may be connected to ring assembly 14, 16, 106, 108, 232 and/or ring segments 32, 33. The clamp 200 may be used to engage bone connection elements (e.g., pins, screw or wires) to ring assembly 14, 16, 106, 108, 232 and/or ring segments 32, 33. The clamp 200 may include a base 202, a first vise plate 204, a second vise plates 206, and a fastener (e.g., a bolt 212 or screw) which may connect the vise plates 204, 206 to the base 202. The base 202 may have a bore 230 sized and configured to receive a distal end 212a of the bolt 212. The bore 230 may be threaded to engage the threaded portion 224 of the bolt 212. In another embodiment, the threaded portion 224 of the bolt 212 may be positioned through the base 202, which may be threaded or unthreaded, and a nut (not shown) may be positioned thereon to hold the bolt 212 to the base 202.

The body 202 may also have a recess (not shown) or other engagement features so that the body 202 and, consequently, the clamp 200 may be connected to a ring assembly or segment. As shown in FIG. 12, a rod 234 may be operably connected to the base 202. In one embodiment, the recess of the base 202 may be threaded and the rod 234 may be threaded to engage the threads of the recess. In other embodiments, the rod 234 may be threaded or unthreaded and maybe be permanently affixed to the base 202, for example, by welding. In some embodiments, the base 202 may be connected directly to a ring assembly 14, 16, 106, 108, 232 or segment 32, 33. Those skilled in the art will appreciate the clamp 200 may be connected to a ring assembly or ring segment using various removable or non-removable connection means including, for example, screws, bolts, nuts, clamps, welds, rivets, or any other suitable attachment means.

The vise plates 204, 206 may have an opening 204a, 206a, respectively, through which the bolt 212 may be passed. In this way, the vise plates 204, 206 may be secured between the head 220 of bolt 212 and base 202. Each vise plates 204, 206 may also have a receiving portion 216 for receiving a bone pin, wire or screw therein such as shown in FIG. 12. As illustrated in FIG. 12, a bone pin 218 may be held in the receiving portions 216 of the vise plates 204, 206 and may be positioned along the axis 216a of the receiving portions 216. In some embodiments, one vise plate 204, 206 may have a receiving portion 216 and the other vise plate 204, 206 may have no receiving portion 216. The clamp 200 may sized and configured to receive bone connection elements of different sizes (e.g., different clamp 200 may have different sized vise plates 204, 206 and/or different sized receiving portions 216).

The vise plate 204 may have a recessed portion 219 which may be sized and configured to receive a biasing member (e.g., spring 210) therein. Biasing member 210 (e.g., coil spring, wave washer, radial spring) may be positioned between the first vise plate 204 and the head 220 of the bolt 212 such that when the vise plates 204, 206 are held between the head 220 of the bolt 212 and the base 202, the vise plates 204, 206 may be biased towards each other. In this way, when the bolt 212 is connected to the base 202 but not completely tightened thereto, a bone connection element may be clipped or snapped between the vise plates 204, 206 by inserting the bone connection element into the receiving portions 216 of the vise plates 204, 206 in a direction which may be at an angle (e.g., perpendicular or transverse) with respect to the axis 200a of the clamp 200. Such a construction may allow a bone connection element to be provisionally held between the vise plates 204, 206 before the bolt 212 is completely tightened in the base 202. In another embodiment, a biasing member may be positioned between the vise plates 204, 206 so that the vise plates 204, 206 may be biased away from each other. Such a configuration may enable an operator to insert a bone connection element between vise plates 206, 206 with minimal resistance.

Moreover, the vise plates 204, 206 may have features to facilitate proper alignment of the vise plates 204, 206. For example, the second vise plate 206 may have at least one protrusion 214 extending therefrom which may be receiving in at least one recess (not shown) in the first vise plate 204. In this manner, the vise plates 204, 206 can both rotate together to orient the receiving portions 216 but cannot rotate with respect to each other or may only be configured to permit limited rotational movement with respect to each other dependant upon the fit of the protrusion 214 in the recess. In another embodiment, the first vise plate 204 may have one or more protrusions 214 and the second vise plate 206 may have one or more recesses for receiving one or more protrusions 214. Such a configuration may allow the vise plates 204, 206 to move axially, but not rotationally, with respect to each other. One will appreciate that various other pins, protrusions, indentations, couplers or other alignment features may be used.

In order to prevent the vise plates 204, 206 from rotating relative to the base 202, the second vise plate 206 may have an engagement portion 226 (e.g., serrations or a knurled surface) which may engage a corresponding engagement portion 228 (e.g., serrations or a knurled surface) of the base 202. A biasing member 208 (e.g., radial spring 208) may be positioned between the base 202 and the second vise plate 206 so as to keep the engagement portions 226, 228 from engaging each other prior to tightening of the bolt 212 to the base 202. In this way, when bolt 212 is provisionally (i.e., not fully) tightened to the base 202, the vise plates 204, 206 may rotate relative to the base 202. In the embodiment shown in FIG. 11, when the bolt 212 overcomes the biasing force of the radial spring 208, the radial spring 208 may be compressed and/or may flatten. Upon tightening the bolt 212 to the base 202, the engagement portions 226, 228 may engage each other and may fix the base 202 relative to the vise plates 204, 206 (i.e., the base 202 and the vise plates 204, 206 may not rotate relative to each other). The biasing member 208 may provide a biasing force which may keep the engagement portions 226, 228 apart until bolt 212 is tightened to overcome the biasing force. As shown in FIG. 11, the radial spring 208 may be a helical coil.

In order to tighten the bolt 212, the head of the bolt 212 may have a gripping portion 220a (e.g., serrated or knurled portion) which may facilitate hand-tightening of the bolt 212. Alternatively or in addition, the head 220 may have one or more surfaces 222, which may be flat (planar), or other features to facilitate engagement of a wrench or other tool. Those skilled in the art will appreciate that other clamps may also be used with the external fixation system shown and described.

Any or all of the devices describe herein such as, for example, the ring assemblies 14, 16; ring segments 32, 33; linear distractor 18; nut 60; tightening member 72; rod 20, 116, 132, 134; washers 96, 98; angular distractor 102; angular separation assemblies 104; clamp 200; bone connection elements (e.g., pins, wires and/or screws), fasteners (e.g., nuts, bolts, rivets, etc) and/or components of any of the devices may be provided in sets or kits so that the a surgeon may select various combinations of components to create an external fixation system which is configured specifically for the particular needs of a patient and the bone fracture/deformity. It should be noted that one or more of each device and/or their components may be provided in a kit or system. In some kits or sets, the same device may be provided in different shapes and/or sizes (e.g., multiple rods of different lengths and/or multiple clamps, distractors, nuts of different sizes).

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are therefore to be considered in all respects as illustrative and not restrictive, the scope of the invention being indicated by the appended claims, and not limited to the foregoing description.

What is claimed is:

1. An external fixation system, comprising:
a first ring member and a second ring member;
at least one distractor disposed between said first and second ring members, the distractor being configured to move the first and second ring members relative to each other; and
at least one clamp operably connected to at least one ring member comprising:
a base including a coupling element attaching the clamp to the at least one ring member and an engagement portion;
a first vise plate and a second vise plate, the vise plates being sized and configured to receive a bone connection element therebetween, wherein the second vise plate has an engagement portion for engaging the engagement portion on the base in order to prevent the first vise plate and second vise plate from rotating relative to the base;
a fastener positionable through the first and second vise plates to engage a respectively sized opening formed in the base;
a first biasing member positioned between a head of the fastener and the first vise plate, the first biasing member being compressible; and
a second biasing member positioned between the second vise plate and the base for separating the engagement portions of the second vise plate and the base, the second biasing member being compressible to allow the engagement portions to engage each other upon tightening of the fastener to the base to engage each other upon tightening of the fastener to the base;
wherein the coupling element includes a bottom surface and a top surface, and a first axis extending there-between, the base is a protrusion extending from the to surface, the opening of the base is open along a second axis, wherein the first and second axis are substantially perpendicular to each other.

2. The system of claim 1, wherein at least one of the first and second ring members comprises multiple ring segments.

3. The system of claim 1, wherein at least one of the first and second ring members is a ring assembly which comprises at least two ring segments.

4. The system of claim 1, wherein the bone connection element is selected from the group consisting of a pin, a wire and a screw.

5. The system of claim 1, wherein the distractor comprises:
a body portion having a proximal end, a distal end and an opening therein, wherein the proximal end of the body portion is operable connected to one of the first and second ring members;
a threaded member having a proximal end and a distal end, the threaded member being positioned within the opening of the body portion and being operably attached to the other of the first and second ring members; and
a knob having a bore therethrough for receiving the threaded member, the knob rotatably coupled to the distal end of the body portion, wherein rotation of the knob causes the rod to move axially within the knob and the opening of the body portion so that the first and second ring members move relative to each other.

6. The system of claim 5, wherein said body portion further comprises a gauge for determining changes in position of the threaded member relative to the body portion.

7. The system of claim 6, wherein the body portion further comprises a window for viewing the position of the proximal end of said threaded member within the body portion.

8. The system of claim 5, wherein the distractor comprises a detent assembly operably associated with the knob, the body portion comprises one or more indentations positioned at predetermined intervals around an outer surface of the body portion, and the knob comprises at least one protrusion engageable with one or more indentations as the knob is rotated about the body portion such that an operator is provided with at least one of tactile and audible feedback.

9. The system of claim 8, wherein the knob further comprises a plurality of markings, each marking designating a discreet increment of movement between indentations.

10. The system of claim 5, wherein rotation of the knob in a first direction moves the first and second ring members together, and rotation of the knob in a second direction moves the first and second ring member apart.

11. The system of claim 1, wherein the second biasing member is a radial spring.

12. The system of claim 1 wherein one of the first and second vise plates of the at least one clamp comprises at least one protrusion and the other of the first and second vise plate having at least one recess for receiving the at least one protrusion such that the first and second vise plates can move axially, but has limited rotational movement relative to each other.

13. The system of claim 1, further comprising a nut having a first end, a second end, a central axis and a bore extending from the first to the second end, the bore having an axis which is oblique relative to the axis of the nut.

14. The system of claim 13, wherein the bore comprises a first threaded portion proximate the first end, a second threaded portion proximate the second end and an unthreaded portion between the first and second ends.

15. A kit for constructing an external fixation system, comprising:
at least two ring members;
at least one distractor disposed between at least two ring members, the distractor being configured to move the at least two ring members relative to each other; and
at least one clamp operably connected to at least one ring member comprising:
a base including a coupling element attaching the clamp to the at least one ring member and an engagement portion;
a first vise plate and a second vise plate, the vise plates being sized and configured to receive a bone connection element therebetween, wherein the second vise plate has an engagement portion for engaging the engagement portion on the base in order to prevent the first vise plate and second vise plate from rotating relative to the base;
a fastener positionable through the first and second vise plates to engage a respectively sized opening formed in the base;
a first biasing member positioned between a head of the fastener and the first vise plate, the first biasing member being compressible; and
a second biasing member positioned between the second vise plate and the base for separating the engagement portions of the second vise plate and the base, the second biasing member being compressible to allow the engagement portions to engage each other upon tightening of the fastener to the base to engage each other upon tightening of the fastener to the base;
wherein the coupling element includes a bottom surface and a top surface, and a first axis extending there-between, the base is a protrusion extending from the to surface, the opening of the base is open along a second axis, wherein the first and second axis are substantially perpendicular to each other.

16. The kit of claim 15 further comprising a plurality of bone connection elements.

17. The kit of claim 15 wherein the at least one distractor comprises:
a body portion having a proximal end, a distal end and an opening therein, wherein the proximal end of the body portion is operable connected to one of the at least two ring members;
a threaded member having a proximal end and a distal end, the threaded member being moveable within the opening of the body portion and being operably attached to the other of the at least two ring members; and
a knob having an opening therethrough for receiving the threaded member, the knob rotatably coupled to the distal end of the body portion, wherein rotation of the knob causes the rod to move axially within the knob and the opening of the body portion so that the at least two ring members move relative to each other.

18. The kit of claim 17 wherein one of the at least one distractor is an angular distractor.

* * * * *